US010457977B2

(12) United States Patent
Weitz et al.

(10) Patent No.: US 10,457,977 B2
(45) Date of Patent: *Oct. 29, 2019

(54) PARTICLE-ASSISTED NUCLEIC ACID SEQUENCING

(71) Applicant: President and Fellows of Harvard College, Cambridge, MA (US)

(72) Inventors: David A. Weitz, Bolton, MA (US); Adam R. Abate, San Francisco, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 156 days.

This patent is subject to a terminal disclaimer.

(21) Appl. No.: 15/427,511

(22) Filed: Feb. 8, 2017

(65) Prior Publication Data

US 2017/0183715 A1    Jun. 29, 2017

Related U.S. Application Data

(63) Continuation of application No. 14/262,895, filed on Apr. 28, 2014, now abandoned, which is a
(Continued)

(51) Int. Cl.
*C12Q 1/68* (2018.01)
*C12Q 1/6809* (2018.01)
(Continued)

(52) U.S. Cl.
CPC ...... *C12Q 1/6809* (2013.01); *B01L 3/502761* (2013.01); *C12Q 1/6834* (2013.01);
(Continued)

(58) Field of Classification Search
USPC ....... 435/6.1, 6.11, 6.12, 91.1, 91.2; 436/94, 436/501; 536/23.1, 24.3, 24.33, 25.3,
(Continued)

(56) References Cited

U.S. PATENT DOCUMENTS 5,149,625 A   9/1992  Church et al.
5,202,231 A   4/1993  Drmanac et al.
(Continued)

FOREIGN PATENT DOCUMENTS

EP   0 249 007 A2   12/1987
EP   1 019 496 B1   9/2004
(Continued)

OTHER PUBLICATIONS

Extended European Search Report dated Jan. 19, 2018 for Application No. EP 16197694.9.
(Continued)

*Primary Examiner* — Frank W Lu
(74) *Attorney, Agent, or Firm* — Wolf, Greenfield & Sacks, P.C.

(57) ABSTRACT

This invention generally relates to particle-assisted nucleic acid sequencing. In some embodiments, sequencing may be performed in a microfluidic device, which can offer desirable properties, for example, minimal use of reagents, facile scale-up, and/or high throughput. In one embodiment, a target nucleic acid may be exposed to particles having nucleic acid probes. By determining the binding of the particles to the target nucleic acid, the sequence of the target nucleic acid (or at least a portion of the target nucleic acid) can be determined. The target nucleic acid may be encapsulated within a fluidic droplet with the particles having nucleic acid probes, in certain instances. In some cases, the sequence of the target nucleic acid may be determined, based on binding of the particles, using sequencing by hybridization (SBH) algorithms or other known techniques.

20 Claims, 7 Drawing Sheets
Specification includes a Sequence Listing.

Related U.S. Application Data continuation of application No. 13/139,326, filed as application No. PCT/US2009/006649 on Dec. 18, 2009, now Pat. No. 8,748,094.

(60) Provisional application No. 61/139,207, filed on Dec. 19, 2008.

(51) Int. Cl.
    *C12Q 1/6869* (2018.01)
    *B01L 3/00* (2006.01)
    *C12Q 1/6834* (2018.01)
    *C12Q 1/6874* (2018.01)

(52) U.S. Cl.
    CPC ......... *C12Q 1/6869* (2013.01); *C12Q 1/6874* (2013.01); *B01L 2200/10* (2013.01)

(58) Field of Classification Search
    USPC ..................................................... 536/25.32
    See application file for complete search history.

(56) References Cited

U.S. PATENT DOCUMENTS

| | | | |
|---|---|---|---|
| 5,436,130 A | 7/1995 | Mathies et al. | |
| 5,512,131 A | 4/1996 | Kumar et al. | |
| 5,695,940 A | 12/1997 | Drmanac et al. | |
| 5,736,330 A | 4/1998 | Fulton | |
| 5,834,252 A | 11/1998 | Stemmer et al. | |
| 5,851,769 A | 12/1998 | Gray et al. | |
| 6,046,003 A | 4/2000 | Mandecki | |
| 6,051,377 A | 4/2000 | Mandecki | |
| 6,057,107 A | 5/2000 | Fulton | |
| 6,103,537 A | 8/2000 | Ullman et al. | |
| 6,297,006 B1 | 10/2001 | Drmanac et al. | |
| 6,297,017 B1 | 10/2001 | Schmidt et al. | |
| 6,355,198 B1 | 3/2002 | Kim et al. | |
| 6,361,950 B1 | 3/2002 | Mandecki | |
| 6,432,360 B1 | 8/2002 | Church | |
| 6,485,944 B1 | 11/2002 | Church et al. | |
| 6,511,803 B1 | 1/2003 | Church et al. | |
| 6,524,456 B1 | 2/2003 | Ramsey et al. | |
| 6,586,176 B1 | 7/2003 | Trnovsky et al. | |
| 6,632,606 B1 | 10/2003 | Ullman et al. | |
| 6,670,133 B2 | 12/2003 | Knapp et al. | |
| 6,767,731 B2 | 7/2004 | Hannah | |
| 6,800,298 B1 | 10/2004 | Burdick et al. | |
| 6,806,058 B2 | 10/2004 | Jesperson et al. | |
| 6,913,935 B1 | 7/2005 | Thomas | |
| 6,929,859 B2 | 8/2005 | Chandler et al. | |
| 7,041,481 B2 | 5/2006 | Anderson et al. | |
| 7,129,091 B2 | 10/2006 | Ismagilov et al. | |
| 7,268,167 B2 | 9/2007 | Higuchi et al. | |
| 7,425,431 B2 | 9/2008 | Church et al. | |
| 7,536,928 B2 | 5/2009 | Kazuno | |
| 7,604,938 B2 | 10/2009 | Takahashi et al. | |
| 7,638,276 B2 | 12/2009 | Griffiths et al. | |
| 7,708,949 B2 | 5/2010 | Stone et al. | |
| RE41,780 E | 9/2010 | Anderson et al. | |
| 7,799,553 B2 | 9/2010 | Mathies et al. | |
| 7,968,287 B2 | 6/2011 | Griffiths et al. | |
| 8,252,539 B2 | 8/2012 | Quake et al. | |
| 8,273,573 B2 | 9/2012 | Ismagilov et al. | |
| 8,278,071 B2 | 10/2012 | Brown et al. | |
| 8,304,193 B2 | 11/2012 | Ismagilov et al. | |
| 8,329,407 B2 | 12/2012 | Ismagilov et al. | |
| 8,748,094 B2 | 6/2014 | Weitz et al. | |
| 8,748,102 B2 | 6/2014 | Berka et al. | |
| 8,765,380 B2 | 7/2014 | Berka et al. | |
| 8,822,148 B2 | 9/2014 | Ismagilov et al. | |
| 8,871,444 B2 | 10/2014 | Griffiths et al. | |
| 8,889,083 B2 | 11/2014 | Ismagilov et al. | |
| 9,017,948 B2 | 4/2015 | Agresti et al. | |
| 9,029,083 B2 | 5/2015 | Griffiths et al. | |
| 9,029,085 B2 | 5/2015 | Agresti et al. | |
| 9,056,289 B2 | 6/2015 | Weitz et al. | |
| 9,068,210 B2 | 6/2015 | Agresti et al. | |
| 9,797,010 B2 | 10/2017 | Weitz et al. | |
| 9,816,121 B2 | 11/2017 | Agresti et al. | |
| 9,850,526 B2 | 12/2017 | Agresti et al. | |
| 10,221,437 B2 | 3/2019 | Weitz et al. | |
| 2001/0020588 A1 | 9/2001 | Adourian et al. | |
| 2001/0044109 A1 | 11/2001 | Mandecki | |
| 2002/0034737 A1 | 3/2002 | Drmanac | |
| 2002/0034747 A1 | 3/2002 | Bruchez et al. | |
| 2002/0051992 A1 | 5/2002 | Bridgham et al. | |
| 2002/0058332 A1 | 5/2002 | Quake et al. | |
| 2002/0092767 A1 | 7/2002 | Bjornson et al. | |
| 2002/0179849 A1 | 12/2002 | Maher et al. | |
| 2003/0008285 A1 | 1/2003 | Fischer | |
| 2003/0008323 A1 | 1/2003 | Ravkin et al. | |
| 2003/0028981 A1 | 2/2003 | Chandler et al. | |
| 2003/0039978 A1 | 2/2003 | Hannah | |
| 2003/0044777 A1 | 3/2003 | Beattie | |
| 2003/0044836 A1 | 3/2003 | Levine et al. | |
| 2003/0099954 A1 | 5/2003 | Miltenyi et al. | |
| 2003/0104466 A1 | 6/2003 | Knapp et al. | |
| 2003/0108897 A1 | 6/2003 | Drmanac | |
| 2003/0170698 A1 | 9/2003 | Gascoyne et al. | |
| 2003/0182068 A1 | 9/2003 | Battersby et al. | |
| 2003/0207260 A1 | 11/2003 | Trnovsky et al. | |
| 2003/0215862 A1 | 11/2003 | Parce et al. | |
| 2004/0063138 A1 | 4/2004 | McGinnis et al. | |
| 2004/0132122 A1 | 7/2004 | Banerjee et al. | |
| 2005/0019839 A1 | 1/2005 | Jesperson et al. | |
| 2005/0042625 A1 | 2/2005 | Schmidt et al. | |
| 2005/0136486 A1 | 6/2005 | Haushalter | |
| 2005/0153290 A1 | 7/2005 | Van Beuningen et al. | |
| 2005/0172476 A1 | 8/2005 | Stone et al. | |
| 2005/0181379 A1 | 8/2005 | Su et al. | |
| 2005/0221339 A1 | 10/2005 | Griffiths et al. | |
| 2005/0244850 A1 | 11/2005 | Huang et al. | |
| 2005/0287572 A1 | 12/2005 | Mathies et al. | |
| 2006/0020371 A1 | 1/2006 | Ham et al. | |
| 2006/0073487 A1 | 4/2006 | Oliver et al. | |
| 2006/0078888 A1 | 4/2006 | Griffiths et al. | |
| 2006/0153924 A1 | 7/2006 | Griffiths et al. | |
| 2006/0163385 A1 | 7/2006 | Link et al. | |
| 2006/0240506 A1 | 10/2006 | Kushmaro et al. | |
| 2006/0257893 A1 | 11/2006 | Takahashi et al. | |
| 2006/0292583 A1 | 12/2006 | Schneider et al. | |
| 2007/0003442 A1 | 1/2007 | Link et al. | |
| 2007/0020617 A1 | 1/2007 | Trnovsky et al. | |
| 2007/0054119 A1 | 3/2007 | Garstecki et al. | |
| 2007/0092914 A1 | 4/2007 | Griffiths et al. | |
| 2007/0172873 A1 | 7/2007 | Brenner et al. | |
| 2007/0195127 A1 | 8/2007 | Ahn et al. | |
| 2007/0228588 A1 | 10/2007 | Noritomi et al. | |
| 2007/0264320 A1 | 11/2007 | Lee et al. | |
| 2008/0003142 A1 | 1/2008 | Link et al. | |
| 2008/0004436 A1 | 1/2008 | Tawfik et al. | |
| 2008/0014589 A1 | 1/2008 | Link et al. | |
| 2009/0012187 A1 | 1/2009 | Chu et al. | |
| 2009/0035770 A1 | 2/2009 | Mathies et al. | |
| 2009/0068170 A1 | 3/2009 | Weitz et al. | |
| 2009/0131543 A1 | 5/2009 | Weitz et al. | |
| 2009/0197248 A1 | 8/2009 | Griffiths et al. | |
| 2009/0197772 A1 | 8/2009 | Griffiths et al. | |
| 2009/0286687 A1 | 11/2009 | Dressman et al. | |
| 2010/0022414 A1 | 1/2010 | Link et al. | |
| 2010/0055677 A1 | 3/2010 | Colston et al. | |
| 2010/0130369 A1 | 5/2010 | Shenderov et al. | |
| 2010/0136544 A1 | 6/2010 | Agresti et al. | |
| 2010/0137163 A1 | 6/2010 | Link et al. | |
| 2010/0173394 A1 | 7/2010 | Colston, Jr. et al. | |
| 2010/0210479 A1 | 8/2010 | Griffiths et al. | |
| 2011/0086780 A1 | 4/2011 | Colston et al. | |
| 2011/0092392 A1 | 4/2011 | Colston et al. | |
| 2011/0160078 A1 | 6/2011 | Fodor et al. | |
| 2011/0218123 A1 | 9/2011 | Weitz et al. | |
| 2011/0267457 A1 | 11/2011 | Weitz et al. | |
| 2012/0010098 A1 | 1/2012 | Griffiths et al. | |
| 2012/0010107 A1 | 1/2012 | Griffiths et al. | |
| 2012/0015382 A1 | 1/2012 | Weitz et al. | |

(56) References Cited

U.S. PATENT DOCUMENTS

| | | |
|---|---|---|
| 2012/0015822 A1 | 1/2012 | Weitz et al. |
| 2012/0190032 A1 | 7/2012 | Ness et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2013/0079231 A1 | 3/2013 | Pushkarev et al. |
| 2013/0109575 A1 | 5/2013 | Kleinschmidt et al. |
| 2013/0157899 A1 | 6/2013 | Adler et al. |
| 2013/0210639 A1 | 8/2013 | Link et al. |
| 2013/0274117 A1 | 10/2013 | Church et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0227684 A1 | 8/2014 | Hindson et al. |
| 2014/0235506 A1 | 8/2014 | Hindson et al. |
| 2014/0303039 A1 | 10/2014 | Weitz et al. |
| 2014/0378349 A1 | 12/2014 | Hindson et al. |
| 2015/0005200 A1 | 1/2015 | Hindson et al. |
| 2015/0314292 A1 | 11/2015 | Weitz et al. |
| 2015/0336068 A1 | 11/2015 | Weitz et al. |
| 2015/0336069 A1 | 11/2015 | Weitz et al. |
| 2015/0336070 A1 | 11/2015 | Weitz et al. |
| 2015/0336071 A1 | 11/2015 | Weitz et al. |
| 2015/0336072 A1 | 11/2015 | Weitz et al. |
| 2015/0337371 A1 | 11/2015 | Weitz et al. |
| 2015/0353999 A1 | 12/2015 | Agresti et al. |
| 2017/0183701 A1 | 6/2017 | Agresti et al. |
| 2018/0023109 A1 | 1/2018 | Weitz et al. |
| 2018/0057875 A1 | 3/2018 | Weitz et al. |
| 2018/0119212 A1 | 5/2018 | Weitz et al. |
| 2018/0171373 A1 | 6/2018 | Weitz et al. |

FOREIGN PATENT DOCUMENTS

| | | |
|---|---|---|
| EP | 1 482 036 B1 | 10/2007 |
| EP | 1 594 980 B1 | 11/2009 |
| EP | 1 967 592 B1 | 4/2010 |
| EP | 2 258 846 A2 | 12/2010 |
| EP | 2 145 955 B1 | 2/2012 |
| EP | 2145955 B1 | 2/2012 |
| EP | 1 905 828 B1 | 8/2012 |
| EP | 1905828 B1 | 8/2012 |
| EP | 1 908 832 B1 | 12/2012 |
| EP | 1908832 B1 | 12/2012 |
| EP | 2 540 389 A1 | 1/2013 |
| JP | S59-049832 A2 | 3/1984 |
| JP | 2004-361291 A | 12/2004 |
| JP | 2006-507921 A | 3/2006 |
| JP | 2006-289250 A | 10/2006 |
| JP | 2007-268350 A | 10/2007 |
| JP | 2007-298327 A | 11/2007 |
| JP | 2009-208074 A2 | 9/2009 |
| WO | WO 96/29629 A2 | 9/1996 |
| WO | WO 96/41011 A1 | 12/1996 |
| WO | WO 99/09217 A1 | 2/1999 |
| WO | WO 99/52708 A1 | 10/1999 |
| WO | WO 00/08212 A1 | 2/2000 |
| WO | WO 00/26412 A1 | 5/2000 |
| WO | WO 00/50172 A1 | 8/2000 |
| WO | WO 00/56937 A2 | 9/2000 |
| WO | WO 01/14589 A2 | 3/2001 |
| WO | WO 01/89787 A2 | 11/2001 |
| WO | WO 02/31203 A2 | 4/2002 |
| WO | WO 02/086148 A2 | 10/2002 |
| WO | WO 2004/002627 A2 | 1/2004 |
| WO | WO 2004/087308 A1 | 10/2004 |
| WO | WO 2004/088314 A1 | 10/2004 |
| WO | WO 2004/091763 A2 | 10/2004 |
| WO | WO 2004/102204 A1 | 11/2004 |
| WO | WO 2004/103565 A2 | 12/2004 |
| WO | WO 2005/021151 A1 | 3/2005 |
| WO | WO 2005/040406 A1 | 5/2005 |
| WO | WO 2005/049787 A2 | 6/2005 |
| WO | WO 2005/082098 A2 | 9/2005 |
| WO | WO 2006/078841 A1 | 7/2006 |
| WO | WO 2006/096571 A2 | 9/2006 |
| WO | WO 2007/001448 A2 | 1/2007 |
| WO | WO 2007/002490 A2 | 1/2007 |
| WO | WO 2007/024840 A2 | 3/2007 |
| WO | WO 2007/081385 A2 | 7/2007 |
| WO | WO 2007/081387 A1 | 7/2007 |
| WO | WO 2007/089541 A2 | 8/2007 |
| WO | WO 2007/114794 A1 | 10/2007 |
| WO | WO 2007/121489 A2 | 10/2007 |
| WO | WO 2007/133710 A2 | 11/2007 |
| WO | WO 2007/138178 A2 | 12/2007 |
| WO | WO 2007/139766 A2 | 12/2007 |
| WO | WO 2007/140015 A2 | 12/2007 |
| WO | WO 2007/149432 A2 | 12/2007 |
| WO | WO 2008/021123 A1 | 2/2008 |
| WO | WO 2008/091792 A2 | 7/2008 |
| WO | WO 2008/102057 A1 | 8/2008 |
| WO | WO 2008/109176 A2 | 9/2008 |
| WO | WO 2008/134153 A1 | 11/2008 |
| WO | WO 2009/005680 A1 | 1/2009 |
| WO | WO 2009/011808 A1 | 1/2009 |
| WO | WO 2009/085215 A1 | 7/2009 |
| WO | WO 2010/151776 A2 | 12/2010 |
| WO | WO 2011/056546 A1 | 5/2011 |
| WO | WO 2012/048341 A1 | 4/2012 |
| WO | WO 2013/177220 A1 | 11/2013 |

OTHER PUBLICATIONS

Office Action dated May 15, 2017 for U.S. Appl. No. 14/721,558.
Office Action dated May 29, 2018 for U.S. Appl. No. 15/884,215.
Notice of Allowance dated Oct. 12, 2018 for U.S. Appl. No. 15/884,215.
Office Action dated May 26, 2017 for U.S. Appl. No. 12/809,120.
Notice of Allowance dated Jul. 11, 2017 for U.S. Appl. No. 12/809,120.
Invitation to Pay Additional Fees for PCT/US2008/003185 dated Oct. 22, 2008.
International Search Report and Written Opinion of the International Searching Authority for International Application No. PCT/US2008/003185, dated Jan. 12, 2009.
International Preliminary Report on Patentability for PCT/US2008/003185 dated Sep. 17, 2009.
International Search Report and Written Opinion of the International Searching Authority for International Application No. PCT/US2008/008563, dated Oct. 29, 2008.
Chinese Office Action dated Jun. 18, 2012 for CN Application No. 200880127116.4.
Chinese Office Action dated May 23, 2013 for Application No. CN 200880127116.4.
Chinese Office Action dated Dec. 24, 2013 for CN Application No. 200880127116.4.
Office Communication dated Dec. 15, 2010 for Application No. EP 08865992.5.
Office Communication dated Jan. 23, 2012 for Application No. EP 08865992.5.
Office Communication dated Apr. 5, 2013 for Application No. EP 08865992.5.
Office Communication dated Aug. 29, 2013 for Application No. EP 08865992.5.
Office Communication dated Apr. 29, 2014 for EP Application No. EP 08865992.5.
Japanese Office Action dated Jul. 17, 2013 for Application No. JP 2010-539498.
Japanese Office Action dated Sep. 2, 2014 for Application No. JP 2010-539498.
International Search Report and Written Opinion of the International Searching Authority for International Application No. PCT/US2008/013912, dated Apr. 3, 2009.
International Preliminary Report on Patentability for PCT/US2008/013912 dated Jul. 1, 2010.
Invitation to Pay Additional Fees for PCT Application PCT/US09/005184 dated May 27, 2010.

(56) References Cited

OTHER PUBLICATIONS

International Search Report and Written Opinion from PCT Application PCT/US09/005184 dated Aug. 16, 2010.
International Preliminary Report on Patentability for PCT Application PCT/US09/005184 dated Mar. 31, 2011.
International Search Report and Written Opinion of the International Searching Authority for International Application No. PCT/US2009/003389, dated Oct. 21, 2009.
International Search Report and Written Opinion of the International Searching Authority for International Application No. PCT/US2009/004037, dated Oct. 2, 2009.
European Office action dated Nov. 7, 2014 for Application No. EP 09804166.8.
Extended European Search Report dated Feb. 9, 2017 for Application No. EP 16197694.9.
International Search Report and Written Opinion for International Application No. PCT/US2009/006649 dated Mar. 10, 2010.
International Preliminary Report on Patentability for International Application No. PCT/US2009/006649 dated Jun. 30, 2011.
Australian Office Action dated Dec. 17, 2013 for Application No. AU 2010315580.
Chinese Office Action dated Dec. 16, 2013 for Application No. CN 201080055990.9.
Chinese Office Action dated Jul. 30, 2014 for Application No. CN 201080055990.9.
Japanese Office Action dated Nov. 19, 2013 for Application No. JP 2012-536941.
Japanese Office Action dated Aug. 5, 2014 for Application No. JP 2012-536941.
International Search Report and Written Opinion from PCT Application PCT/US2010/054050 dated Jan. 31, 2011.
International Preliminary Report on Patentability from PCT Application PCT/US2010/054050 dated May 10, 2012.
Office Action dated Oct. 1, 2012 for U.S. Appl. No. 12/529,926.
Final Office Action dated May 28, 2013 for U.S. Appl. No. 12/529,926.
Interview Summary dated Feb. 12, 2014 for U.S. Appl. No. 12/529,926.
Office Action dated Aug. 6, 2014 for U.S. Appl. No. 12/529,926.
Office Action dated May 20, 2014 for U.S. Appl. No. 14/172,266.
Advisory Action dated Jan. 23, 2015 for U.S. Appl. No. 14/172,266.
Final Office Action dated Nov. 21, 2014 for U.S. Appl. No. 14/172,266.
Office Action dated May 20, 2014 for U.S. Appl. No. 14/172,326.
Final Office Action dated Nov. 20, 2014 for U.S. Appl. No. 14/172,326.
Advisory Action dated Jan. 23, 2015 for U.S. Appl. No. 14/172,326.
Office Action dated Feb. 13, 2017 for U.S. Appl. No. 14/721,58.
Office Action dated Jan. 4, 2010 for U.S. Appl. No. 12/172,186.
Office Action dated Jul. 30, 2014 for U.S. Appl. No. 12/809,120.
Office Action dated Mar. 12, 2015 for U.S. Appl. No. 12/809,120.
Advisory Action dated Jun. 25, 2015 for U.S. Appl. No. 12/809,120.
Office Action dated Mar. 29, 2016 for U.S. Appl. No. 12/809120.
Office Action dated Jul. 20, 2016 for U.S. Appl. No. 12/809,120.
Final Office Action dated Dec. 5, 2013 for U.S. Appl. No. 13/119,470.
Advisory Action dated Mar. 21, 2014 for U.S. Appl. No. 13/119,470.
Office Action dated Jun. 24, 2015 for U.S. Appl. No. 13/119,470.
Office Action dated Jan. 6, 2016 for U.S. Appl. No. 14/812,930.
Office Action dated Feb. 28, 2013 for U.S. Appl. No. 13/139,326.
Advisory Action dated Nov. 20, 2013 for U.S. Appl. No. 13/139,326.
Notice of Allowance dated Jan. 27, 2014 for U.S. Appl. No. 13/139,326.
Office Action dated Apr. 27 2016 for U.S. Appl. No. 14/262,895.
Office Action dated Jan. 6, 2016 for U.S. Appl. No. 14/262,895.
Advisory Action dated Aug. 10, 2016 for U.S. Appl. No. 14/262,895.
Advisory Action dated Nov. 25, 2016 for U.S. Appl. No. 14/262,895.
Office Action dated Sep. 17, 2013 for U.S. Appl. No. 13/503,588.
Office Action dated Feb. 10, 2014 for U.S. Appl. No. 13/503,588.
Advisory Action dated May 16, 2014 for U.S. Appl. No. 13/503,588.
[No Author] Gene Characterization Kits. Stratagene Catalog. Statagene Cloning Systems: Tools and Technology for Lift Sciences. 1988. 3 pages.
[No Author] Microfluidic ChipShop. Microfluidic product catalogue. Mar. 2005.
[No Author] Microfluidic ChipShop. Microfluidic product catalogue. Oct. 2009.
Abate et al., Droplet Based Sequencing. American Physical Society. Presentation. Mar. 12, 2008. 25 pages.
Abate et al., Valve-based flow focusing for drug formation. Appl Phys Lett. 2009;94. 3 pages. (Month not cited on publication).
Agresti, "Selection of ribozymes that catalyse multiple-turnover Diels-Alder cycloadditions by using in vitro compartmentalization", PNAS, 102, 16170-16175 (2005). (Nov. 2005).
Akselband, "Enrichment of slow-growing marine microorganisms from mixed cultures using gel microdrop (GMD) growth assay and fluorescence-activated cell sorting", J. Exp. Marine Biol., 329: 196-205 (2006). (Month not cited on publication).
Akselband, "Rapid mycobacteria drug susceptibility testing using gel microdrop (GMD) growth assay and flow cytometry", J. Microbiol. Methods, 62:181-197 (2005). (Month not cited on publication).
Anna et al., Formation of dispersions using 'flow focusing' in microchannels. Appln Phys Letts. 2003;82(3):364-66. (Jan. 2003).
Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32. (Feb. 2003).
Carroll, "The selection of high-producing cell lines using flow cytometry and cell sorting", Exp. Op. Biol. Therp., 4:11 1821-1829 (2004). (Month not cited on publication).
Chaudhary "A rapid method of cloning functional variable-region antibody genese in *Escherichia coli* as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101. (Month not cited on publication).
Chou, et al. Disposable Microdevices for DNA Analysis and Cell Sorting. Proc. Solid-State Sensor and Actuator Workshop, Hilton Head, SC. Jun. 8-11, 1998; 11-14.
Chu, L., et al., "Controllable Monodisperse Multiple Emulsions," Angew. Chem. Int. Ed., vol. 46, pp. 8970-8974 (2007). (Month not cited on publication).
Clausell-Tormos et al., "Droplet-based microfluidic platforms for the encapsulation and screening of mammalian cells and multicellular organisms", Chem. Biol. 15:427-437 (2008). (May 2008).
De Bruin et al., UBS Investment Research. Q-Series®: DNA Sequencing. UBS Securities LLC. Jul. 12, 2007. 15 pages.
Diaz, R.V., et al., "One-Month sustained release microspheres of 125 I-bovine calcitonin In vitro-in vivo studies," Journal of Controlled Release, vol. 59, pp. 55-62 (1999). (Month not cited on publication).
Doerr, The smallest bioreactor. Nature Methods. 2005; 2(5):326. (May 2005).
Drmanac eta 1., Sequencing by hybridization (SBH): advantages, achievements, and opportunities. Adv Biochem Eng Biotechnol. 2002;77:75-101. (Month not cited on publication).
Fu, "A microfabricated fluorescence-activated cell sorter", Nature Biotech., 17:1109-1111 (1999). (Nov. 1999).
Fulton et al., Advanced multiplexed analysis with the FlowMetrix system. Clin Chem. Sep. 1997;43(9):1749-56.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Ghadessy et al. Directed evolution of polymerase function by compartmentalized self-replication. Proc Natl Acad Sci USA. Apr. 10, 2001; 98(8):4552-7. Epub Mar. 27, 2001.
Griffiths et al., Directed evolution of an extremely fast phosphotriesterase by in vitro compartmentalization. EMBO J. Jan. 2, 2003;22(1):24-35.
He et al., "Selective Encapsulation of Single Cells and Subcellular Organelles into Picoliter- and Femtoliter-Volume Droplets" Anal. Chem 77: 1539-1544 (2005) (Mar. 2005).

(56) References Cited

OTHER PUBLICATIONS

Holtze et al., Biocompatible surfactants for water-in-fluorocarbon emulsions. Lab Chip. Oct. 2008; 8(10):1632-9.
Huebner, "Quantitative detection of protein expression in single cells using droplet microfluidics", Chem. Commun. 1218-1220 (2007). (Month not cited on publication).
Hug et al. Measurement of the number of molecules of a single mRNA species in a complex mRNA preparation. J Theor Biol. Apr. 21, 2003; 221(4):615-24.
Khomiakova et al., [Analysis of perfect and mismatched DNA duplexes by a generic hexanucleotide microchip]. Mol Biol (Mosk). Jul.-Aug. 2003;37(4):726-41. Russian.
Kim et al., Fabrication of monodisperse gel shells and functional microgels in microfluidic devices. Angew Chem Int Ed Engl. Mar. 2007;46(11):1819-22.
Kim, "Fabrication of monodisperse gel shells and functional microgels in microfluidic devices", Angew. Chem., 119:1851-1854 (2007).
Kim, J., et al, "Albumin loaded microsphere of amphiphilic poly-(ethylene glycol)/poly(a-ester) multiblock copolymer," European Journal of Pharmaceutical Sciences, vol. 23, pp. 245-251 (2004). (Month not cited on publication).
Koster et al., "Drop-based microfluidic devices for encapsulation of single cells", Lab on a Chip the Royal Soc. of Chem. 8:1110-1115 (2008). (Month not cited on publication).
Li, Y., et al., "PEGylated PLGA nanoparticles as protein carriers: synthesis, preparation and biodistribution in rats," Journal of Controlled Release, vol. 71, pp. 203-211 (2001). (Month not cited on publication).
Loscertales, Micro/Nano encapsulation via electrified coaxial liquid jets. Science. 2002;295:1695-98. (Mar. 2002).
Love, A microengraving method for rapid selection of single cells producing antigen-specific antibodies. Nature Biotech. Jun. 2006;24(6):703-07.
Mazutis et al., Selective droplet coalescence using microfluidic systems. Lab Chip. Apr. 24, 2012; 12(10):1800-6.
Mirzabekov, "DNA Sequencing by Hybridization—a Megasequencing Method and a Diagnostic Tool?" Trends in Biotechnology 12(1): 27-32 (1994) (Jan. 1994).
Mouritzen et al., Single nucleotide polymorphism genotyping using locked nucleic acid (LNA). Expert Rev Mol Diagn. Jan. 2003;3(1):27-38.
Nguyen, "In situ hybridization to chromosomes stabilized in gel microdrops", Cytometry, 21:111-119 (1995). (Month not cited on publication).
Nisisako et al., Formation of droplets using branch channels in a microfluidic circuit. SICE. Osaka. Aug. 5-7, 2002. 957-959.
Okushima, "Controlled production of monodisperse double emulsions by two-step droplet breakup in microfluidic devices", Langmuir, 20:9905-9908 (2004). (Month not cited on publication).
Perez, C., et al., "Poly(lactic acid)-poly(ethylene glycol) nanoparticles as new carriers for the delivery of plasmid DNA," Journal of Controlled Release, vol. 75, pp. 211-224 (2001). (Month not cited on publication).
Ryan, "Rapid assay for mycobacterial growth and antibiotic susceptibility using gel microdrop and encapsulation", J. Clinical Microbiol., 33:7 1720-1726 (1995). (Jul. 1995).
Schirinzi et al., Combinatorial sequencing-by-hybridization: analysis of the NF1 gene. Genet Test. 2006 Spring;10(1):8-17. (Month not cited on publication).
Schmitt, "Bead-based multiplex genotyping of human papillomaviruses", J. Clinical Microbiol., 44:2 504-512 (2006). (Feb. 2006).
Shah, "Fabrication of monodisperse thermosensitive microgels and gel capsules in microfluidic devices", Soft Matter, 4:2303-2309 (2008). (Month not cited on publication).
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Su et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Taniguchi et al., Chemical reactions in microdroplets by electrostatic manipulation of droplets in liquid media. Lab Chip. Feb. 2002;2(1):19-23. DOI: 10.1039/B108739H.
Tawfik, et al. Man-made cell-like compartments for molecular evolution. Nat Biotechnol. Jul. 1998;16(7):652-6.
Thorsen, et al. Dynamic pattern formation in a vesicle-generating microfluidic device. Physical Review Letters. American Physical Society. 2001; 86(18):4163-4166.
Umbanhowar, et al. Monodisperse emulsion generation via drop break off in a coflowing stream. Langmuir. 2000; 16:347-351.
Van De Hulst et al., Glare points. Appl Opt. Nov. 20, 1991;30(33):4755-63.
Wang et al., Single nucleotide polymorphism discrimination assisted by improved base stacking hybridization using oligonucleotide microarrays. Biotechniques. 2003;35:300-08. (Aug. 2003).
Weaver, "Rapid clonal growth measurements at the single-cell level: gel microdroplets and flow cytometry", Biotechnology, 9:873-877 (1991). (Sep. 1991).
Whitesides, "Soft lithography in biology and biochemistry", Annual Review of Biomedical Engineering, 3:335-373 (2001). (Month not cited on publication).
Xia, "Soft lithography", Annual Review of Material Science, 28:153-184 (1998). (Month not cited on publication).
Zhang, "Combinatorial marking of cells and organelles with reconstituted fluorescent proteins", Cell, 119:137-144 (Oct. 1, 2004).
Zhao, J., et al., "Preparation of hemoglobin-loaded nano-sized particles with porous structure as oxygen carriers," Biomaterials, vol. 28, pp. 1414-1422 (2007). Available online Nov. 2006.
Zimmerman, Microscale production of hybridomas by hypoosmolar electrofusion. Hum Antibod Hybridomas. Jan. 3, 1992:14-18.

PARTICLE-ASSISTED NUCLEIC ACID SEQUENCING

RELATED APPLICATIONS

This application is a continuation of U.S. patent application Ser. No. 14/262,895, entitled "Particle-Assisted Nucleic Acid Sequencing", filed on Apr. 28, 2014 (now abandoned), which is a continuation of U.S. patent application Ser. No. 13/139,326, entitled "Particle-Assisted Nucleic Acid Sequencing", filed on Jun. 13, 2011 (now U.S. Pat. No. 8,748,094), which is a national stage filing under 35 U.S.C. § 371 of International Application No. PCT/US2009/006649, entitled "Particle-Assisted Nucleic Acid Sequencing", filed on Dec. 18, 2009 (published as WO 2010/080134), which claims priority under 35 U.S.C. § 119(e) to U.S. Provisional Application Ser. No. 61/139,207, entitled "Particle-Assisted Nucleic Acid Sequencing," filed on Dec. 19, 2008, the entire contents of each of which are incorporated by reference herein.

GOVERNMENT FUNDING

This invention was made with government support under grant numbers DMR-0602684 and DBI-0649865 awarded by the National Science Foundation. The government has certain rights in the invention.

FIELD OF INVENTION

This invention relates generally to particle-assisted nucleic acid sequencing. In some embodiments, the nucleic acid sequencing is performed in a microfluidic system.

BACKGROUND

There is a need for faster nucleic acid sequencing. Although small fragments of nucleic acids (i.e. about 1000 bases) may be sequenced on a time scale of hours, the sequencing of entire genomes can increase the sequencing time by many orders of magnitude. Existing nucleic acid sequencing methods may be direct (i.e., each base is determined) or indirect (i.e., smaller sequences within a larger sequence are determined and then assembled to reveal the larger sequence). However, current methods such as those that rely on arrays of oligonucleotide probes have made relatively limited progress in decreasing sequencing time. Accordingly, there is a need for improved sequencing methods that increase sequencing throughput.

SUMMARY OF INVENTION

This invention relates generally to particle-assisted nucleic acid sequencing. In some embodiments, the nucleic acid sequencing is performed in a microfluidic system. The subject matter of the present invention involves, in some cases, interrelated products, alternative solutions to a particular problem, and/or a plurality of different uses of one or more systems and/or articles.

In one aspect, the present invention is directed to a method of sequencing a target nucleic acid. In one set of embodiments, the method includes acts of exposing a target nucleic acid to a plurality of particles, at least some of which have nucleic acid probes fastened thereto, and at least partially determining the sequence of the target nucleic acid based on binding of the particles to the target nucleic acid.

The method, according to another sets of embodiments, includes acts of providing a plurality of particles, at least some of which have nucleic acid probes fastened thereto. In some cases, at least some of the particles are distinguishable from some other particles. In one embodiment, the distinguishable particles have distinguishable nucleic acid probes fastened thereto, and in some cases, the nucleic acid probes are different from other nucleic acids probes fastened to other particles. The method may also include acts of exposing a target nucleic acid to the plurality of particles, determining binding of the distinguishable particles to the target nucleic acid, and at least partially determining a sequence of the target nucleic acid based on the binding of the particles.

Another aspect of the invention is directed to a method including acts of providing a plurality of particles, at least some of which have nucleic acid probes fastened thereto, providing a plurality of substantially identical copies of a target nucleic acid, exposing copies of the target nucleic acid to different subsets of the plurality of particles, and for each of the copies, determining binding of the particles to the target nucleic acid.

Still another aspect of the invention is directed to a composition. The composition, according to a first set of embodiments, includes a plurality of particles, at least some of which have nucleic acid probes fastened thereto. In one embodiment, the plurality of particles contains at least 120 unique nucleic acid probe sequences, such that each of the particles contains only one of the nucleic acid probe sequences and is associated with an identification entity.

In another embodiment, the plurality of particles contains at least one unique nucleic acid probe sequence. In certain instance, the nucleic acid probe has a signaling entity attached thereto, such that each of the particles contains only one of the at least one nucleic acid probe sequences and is associated with an identification entity.

Yet another aspect of the invention contemplates a kit. In one set of embodiments, the kit includes a plurality of particles, at least some of which have nucleic acid probes fastened thereto. In one embodiment, the plurality of particles contains at least 120 unique nucleic acid probe sequences, such that each of the particles contains only one of the nucleic acid probe sequences and is associated with an identification entity.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

BRIEF DESCRIPTION OF THE SEQUENCES

SEQ ID NO:1 is a synthetic oligonucleotide having the sequence ATCCGCTTTA;

SEQ ID NO:2 is a synthetic oligonucleotide having the sequence TAGGCGAAATCATC;

SEQ ID NO:3 is a synthetic oligonucleotide having the sequence GTATCCACATGC; and SEQ ID NO:4 is a synthetic oligonucleotide having the sequence ATTAGCATGTGGATACTCCC.

DETAILED DESCRIPTION

This invention generally relates to particle-assisted nucleic acid sequencing. In some embodiments, sequencing may be performed in a microfluidic device, which can offer desirable properties, for example, minimal use of reagents, facile scale-up, and/or high throughput. In one embodiment, a target nucleic acid may be exposed to particles having nucleic acid probes. By determining the binding of the particles to the target nucleic acid, the sequence of the target nucleic acid (or at least a portion of the target nucleic acid) can be determined. The target nucleic acid may be encapsulated within a fluidic droplet with the particles having nucleic acid probes, in certain instances. In some cases, the sequence of the target nucleic acid may be determined, based on binding of the particles, using sequencing by hybridization (SBH) algorithms or other known techniques.

One aspect of the present invention is generally directed to sequencing a target nucleic acid. A target nucleic acid labeled with a signaling entity may be exposed to a plurality of distinguishable particles, distinguishable using various identification entities and having unique nucleic acid probes. By determining the particles that can associate with the target nucleic acid (e.g., by determining the association between a signaling entity of the target nucleic acid and the identification entities associated with the particles), and determining or identifying the nucleic acid probes that are able to associate with the target nucleic acid, the target nucleic acid may be sequenced, using SBH algorithms or other techniques known to those of ordinary skill in the art.

Figure 1:
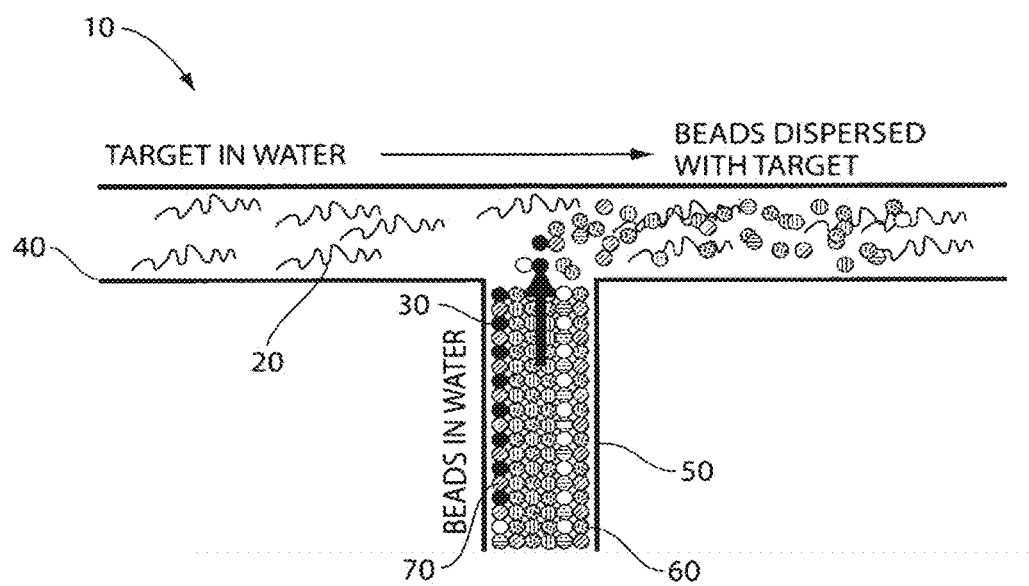
FIG. 1 shows a portion of a sequencing device according to an embodiment of the invention.

A non-limiting example is now described with respect to FIG. 1. This figure shows a sequencing apparatus 10 in which a target nucleic acid sequence 20 is mixed with a library of particles 30 having nucleic acid probes fastened thereto. In this figure, each copy of target nucleic acid sequence 20 found in channel 40 is identical, or at least substantially identical. Optionally, target nucleic acid sequence 20 may have a signaling entity associated therewith. The copies of target nucleic acid sequence 20 are dispersed in a fluid such as an aqueous solution, and the fluid is passed from left to right in channel 40 in this figure. A library of particles 30 having attached nucleic acid probes are passed into channel 40 from the channel 50. As discussed below, the library of particles may comprise a plurality of distinguishable particles, distinguishable using various identification entities and having unique nucleic acid probes on each of the particles, e.g., such that each particle contains only one type of nucleic acid probe, but many identical copies of that probe.

After the library of particles 30 enters from channel 50 into channel 40, the particles are exposed to the labeled target nucleic acid. After the particles enter the channel 40, if a probe on a given particle is at least substantially complimentary to a suitable portion (or all) of the target nucleic acid, then the target nucleic acid will at least partially hybridize to the probe and become associated with the particle, e.g., via non-covalent interactions. However, because the particle contains many copies of the nucleic acid probe on its surface, it can accumulate multiple copies of the labeled target nucleic acid, which may cause multiple copies of the target nucleic acid to become associated with the particle.

The association of the nucleic acid probe and the target nucleic acid can thus be determined. Typically, the target nucleic acid will not associate with all of the particles and all of the nucleic acid probes. Thus, by determining which of the nucleic acid probes were able to associate with the target nucleic acid, the sequence of the target nucleic acid may be determined using known techniques, such as SBH or other techniques discussed below.

As an example, in embodiments where the target nucleic acid is associated with a signaling entity, such as a fluorophore, particles that accumulate the target nucleic acids will also become associated with the signaling entity associated with the target nucleic acids. For instance, in the case of a fluorescent signaling entity, the fluorescence associated with a particle may be proportional to the amount of target nucleic acid associated with that particle. Thus, for example, in FIG. 1, the variations in the shading of the particles in the library of particles 30 denotes variations in the nucleic acid sequence of the attached nucleic acid probes, i.e., a first particle 60 having a first shade may indicate a first particle having a first sequence of nucleic acid probes, while a second particle 70 having a second shade different from the first shade may indicate a second particle having a second sequence of nucleic acid probes, where the second sequence is different in some way from the first sequence.

Figure 2:
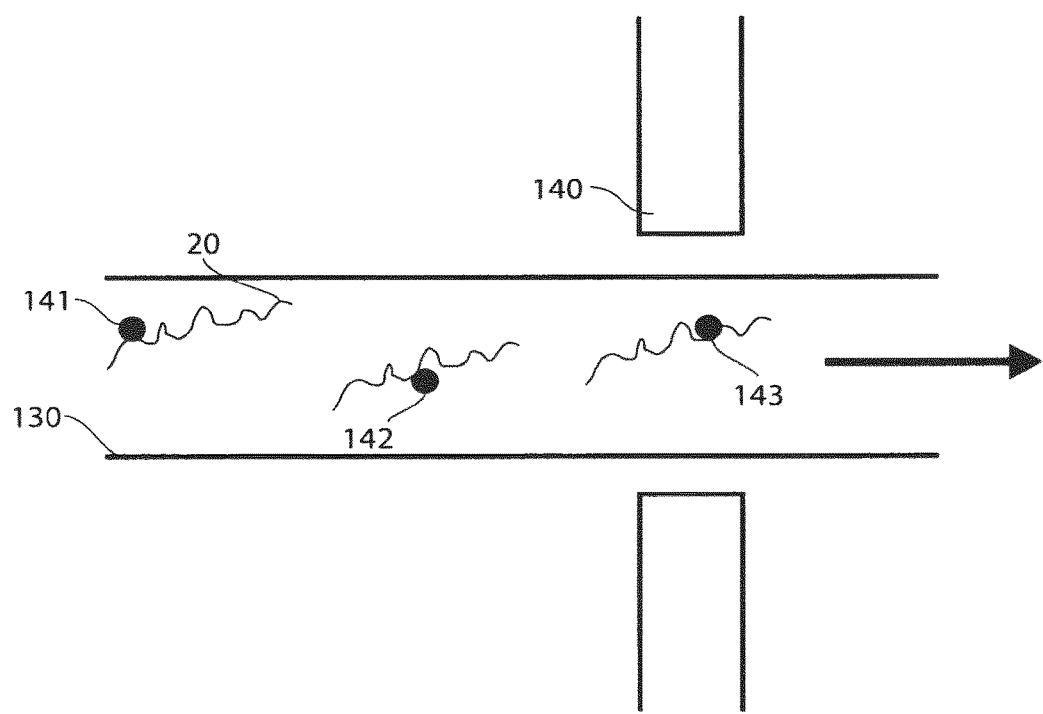
FIG. 2 shows a portion of detection region of a sequencing device, according to another embodiment.

Following hybridization of the target and probe nucleic acids, particles then may flow into an area where the association (if any) between the target and the particles can be determined. For example, the particles may flow past detector 140 as shown in FIG. 2. If target nucleic acid 20 is associated with a signaling entity (not shown) and particles 141, 142, and 143 are each associated with different identification entities (e.g., as described in more detail below), then the determination of the association of the signaling entity with each of the identification entities can be used to determine the association of the target nucleic acid 20 with the particles 141, 142, and/or 143.

Figure 3:
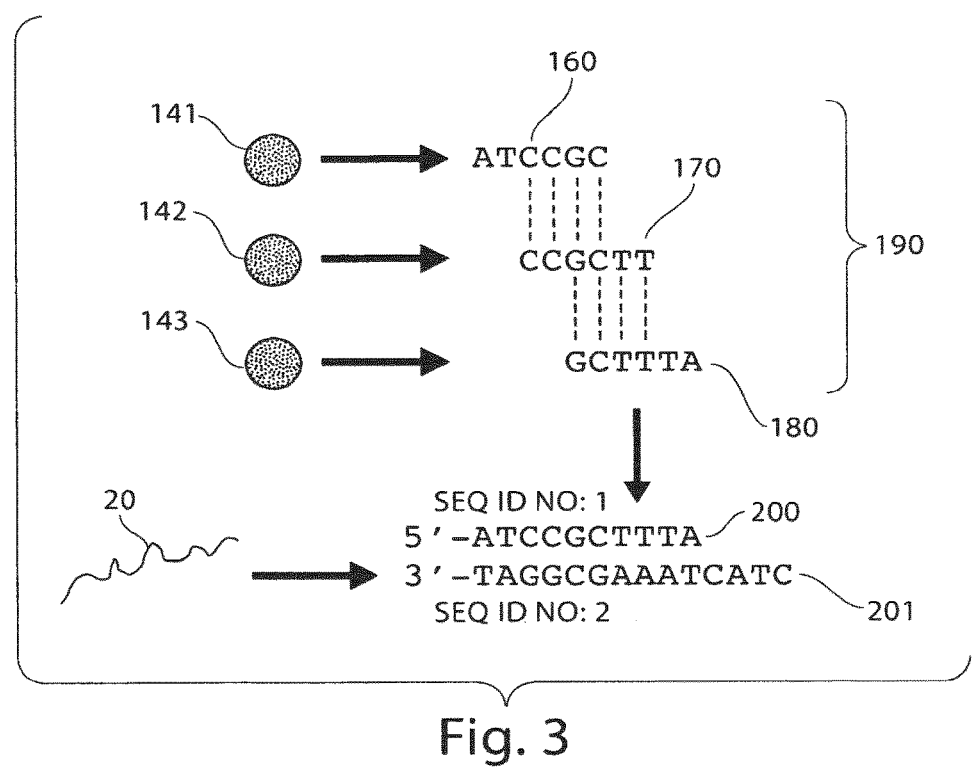
FIG. 3 shows the determination of a nucleic acid sequence, according to yet another embodiment of the invention.

Continuing this example, as shown in FIG. 3, a hybridization spectrum 190 can be produced by identifying particles 141, 142, and 143 as having hybridized with the target nucleic acid 20. For instance, particles 141, 142, and 143 may each be distinguishable in some fashion (e.g., having different fluorescence properties), and the association between particle 141 and sequence 160, particle 142 and sequence 170, and particle 143 and sequence 180 may be recorded, e.g., on a computer. Since, in some embodiments, a particle can contain a single nucleic acid probe fastened to the surface (although the particle may contain many identical copies of this single nucleic acid probe), identification of the set of particles associated with both a signaling entity and an identification entity allows the nucleic acid probe sequences associated with a target nucleic acid to be determined. Thus, as described in more detail below, nucleic acid probe sequences 160, 170, and 180, known to be associated with each respective particle, can be used to reconstruct nucleic acid sequence 200, which is complementary to the corresponding portion of the target nucleic acid sequence 201, as is illustrated in FIG. 3.

In some embodiments, the target nucleic acid and/or particle are in a fluid contained within a device. For example, the target nucleic acid and particle may be combined within a channel of a microfluidic device. In some embodiments, the target nucleic acid and/or particle are contained within a fluidic droplet, which may optionally be contained within a microfluidic device, or other suitable location.

Figure 4:
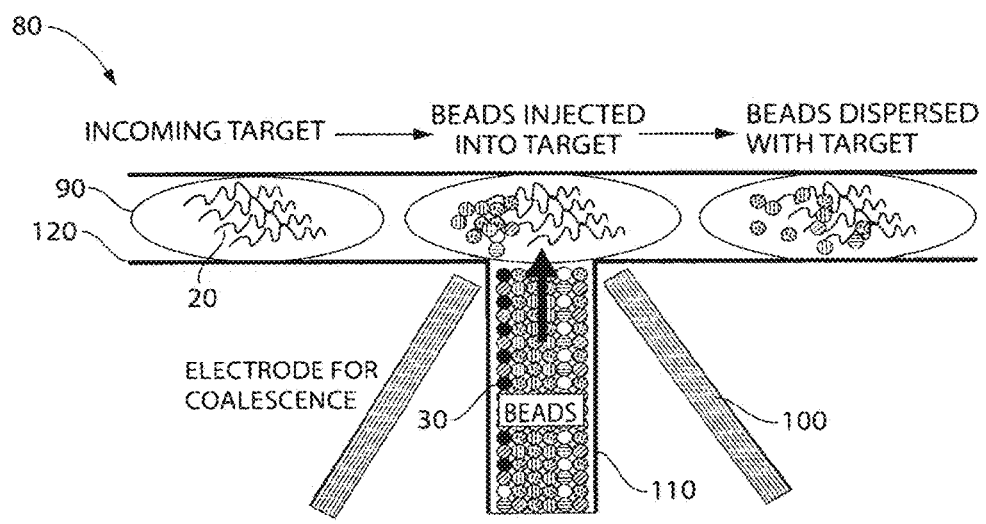
FIG. 4 shows a portion of a droplet-based sequencing device according to still another embodiment of the invention.

Another example is illustrated in FIG. 4, which shows a non-limiting example of a sequencing apparatus 80 that uses particles and fluidic droplets. In this example figure, droplets 90 each contain many essentially identical copies of a target nucleic acid 20, although different droplets may contain different target nucleic acids. The droplets can be merged with the fluid containing the particles using, for example, T-junction channel 110. The droplets in this figure flow from left to right in channel 120, and the probe particles are injected into the droplets from channel 110, e.g., as a plug. The oil interface between the droplets and the probe particles can be broken, e.g., using electro-coalescence using electrodes 100, which allows the probe particles to be injected into the droplet. Other techniques known to those skilled in the art, such as laser light or changing the wettability of a microchannel wall, can be used to merge fluids. The droplet then can contain some or all of the members of particle library 30 and the target nucleic acids. The hybridization process and analysis can proceed as described herein.

Although particular examples of the present invention were discussed above, it should be noted that any combination of the above steps and/or additional steps, may also be used to sequence a target nucleic acid, as discussed in detail below. For instance, the target nucleic acid for which sequence information is desired may be any suitable nucleic acid. For example, the target nucleic acid may be a nucleic acid that encodes a biological entity, such as a protein, an enzyme, an antibody, a receptor, a ribozyme, a ribosome, or the like, and/or a portion thereof. As another non-limiting example, the target nucleic acid may be a regulatory sequence or a non-coding sequence, for instance, a small interfering RNA, a microRNA, a small hairpin RNA, or the like. Non-limiting examples of target nucleic acids (and other types of nucleic acids, as are described herein) include ribonucleic acid (RNA), deoxyribonucleic acid (DNA), or mixtures or copolymers thereof, which may be isolated from natural sources, recombinantly produced, artificially synthesized, etc. For instance, the nucleic acid may be isolated from a cell or a virus, synthesized using traditional chemical synthesis, synthesized using polymerase chain reaction (PCR) technology, or the like. The target nucleic acid can be any number of nucleotides in length, for example, on the order of 25, 50, 60, 64, 70, 80, 90, 100, 200, 400, 800, 1600, 3200, 6400, or even more nucleotides in length. A nucleic acid may contain residues such as the naturally-occurring bases (e.g., adenosine or "A," thymidine or "T," guanosine or "G," cytidine or "C," or uridine or "U"), or other residues, such as methylated residues. The nucleic acid can be single-stranded in some cases to facilitate hybridization.

In some embodiments, a target nucleic acid can also be amplified using nucleic acid amplification techniques, such as PCR (polymerase chain reaction) or the like. Various copies of the target nucleic acid can be labeled with a signaling entity (e.g. a fluorescent dye). The signaling entity may be included within the nucleic acid at any suitable location, for example, at a 5' terminal site of the nucleic acid sequence, a 3' terminal site, or at an internal site within the nucleic acid.

The signaling entity may include, but is not limited to, a fluorescent dye, a chemiluminescent entity, a radioactive label, an isotope such as a non-radioactive isotope or an isotope detectable by mass spectrometry (e.g., an electrophore mass label (EML)), a ligand which can serve as a specific binding partner to a labeled antibody, an enzyme, an antibody which can serve as a specific binding partner for a labeled ligand, an antigen, a group having a specific reactivity, and/or an electrochemically detectable moieties. Non-limiting examples of fluorescent signaling entities include fluorescein, rhodamine, or hexachlorofluorescein. Those of ordinary skill in the art will be aware of other fluorescent entities that are readily commercially available. Yet other examples of signaling entities are discussed in detail herein.

In some cases, the signaling entity may be chosen such that it produces a different signal (or does not produce a signal) when a nucleic acid probe is associated with the target nucleic acid compared to when a nucleic acid probe is not associated with the target nucleic acid.

In some embodiments, however, the target nucleic acid may not have a covalently attached signaling entity. In such instances, binding of the target nucleic acid to a nucleic acid probe fastened to a particle may be determined using other techniques known to those in the art. For example, a signaling entity that detects a double-stranded nucleic acid may be used. For instance, an intercalating signaling entity may be used to determine hybridization between a nucleic acid probe and a target nucleic acid. The fluorscence of fluorescent intercalators can change upon intercalation of a nucleic acid. Generally, intercalation occurs more readily in a double-stranded nucleic acid rather than a single-stranded nucleic acid. In a non-limiting example, hybridization of a target nucleic acid and a nucleic acid probe can be determined by observing the increase in the fluorescence of, for example, ethidium bromide upon intercalation of the ethidium bromide into the nucleic acid probe-target nucleic acid duplex. In some embodiments, the intercalator may be attached to the particle, for example using a linker of sufficient length to allow intercalation of the fluorophore into a duplex. The attached intercalator may then intercalate into a nearby duplex. In other embodiments, the intercalator can be attached to the nucleic acid probe and/or to the target nucleic acid. The intercalator may be attached to the nucleic acid probe and/or the target nucleic acid by a linker of sufficient length to allow intercalation of the intercalator. As another example of a signaling entity that detects double-stranded nucleic acids, a fluorescently-labeled double-stranded nucleic acid binding protein may be used. Such a protein may accumulate on the double-stranded nucleic acids on a particle, thus increasing the fluorescence associated with the particle.

As discussed above, the target nucleic acid may be recognized (hybridized) by one or more nucleic acid probes that can be fastened to a particle. Nucleic acid probes can be used in various embodiments to determine certain sequences within a target nucleic acid. Often, short portions of the target nucleic acid can be associated with a nucleic acid probe, for instance, a sequence of less than 20 residues, less than 15 residues, less than 10 residues, less than 9 residues, less than 8 residues, less than 7 residues, less than 6 residues, less than 5 residues, less than 4 residues, etc. In some embodiments, a nucleic acid probe may contain a relatively short sequence of nucleic acid residues that is able to recognize at least a portion of the target nucleic acid (i.e., the sequences are complementary, or at least substantially complementary), and often has a similar length as the recognized portion of the target nucleic acid. For instance, the nucleic acid probe may have a sequence having a length of less than 20 nucleotides, or less than 10 nucleotides in some cases, or a length such as those described above. In one case, the length of the nucleic acid probe sequence may be four residues. In another case, the length may be five residues. In yet another case, the length may be six residues. The nucleic acid probes may be synthesized using any suitable technique, e.g., solid phase phosphoramidite triester methods. Other methods will be known to those skilled in the art.

The nucleic acid probe sequences within the nucleic acid probe may be contiguous, or the sequence may be noncontiguous. For instance, there may be universal residues or gaps present within the probe sequence. Additionally, secondary structures such as hairpins, loops, etc. may be present in some cases, which may be used to create a noncontiguous sequence. As a non-limiting example, a nucleic acid probe may have a first and second region that are at least substantially complementary to a contiguous sequence of the target nucleic acid and are separated by a third region that is not complementary to the contiguous sequence of the target nucleic acid. The nucleic acid probe may hybridize to the target nucleic acid such that the third region forms a hairpin, thereby allowing the first and second regions to hybridize to the contiguous target nucleic acid sequence in a noncontiguous fashion.

In some cases, a nucleic acid probe may hybridize to a substantially complementary sequence without creating an overhang (i.e., without at least some of the residues within the nucleic acid probe extending past a terminus of the target nucleic acid). Alternatively, in some instances, a nucleic acid probe may hybridize to a target nucleic acid such that at least one residue of the nucleic acid probe extends beyond a terminus of the target nucleic acid.

A nucleic acid probe need not hybridize completely with a target nucleic acid. The hybridization of two nucleic acids and/or nucleic acid analogs can be affected by a variety of factors, and the strength of hybridization of particular residues within a given duplex can be different.

As used herein, a first sequence that is "substantially complementary" to a second sequence is one in which at least 75% of the first and second sequences are complementary (e.g., through Watson-Crick complementary pairing) and/or the sequences have a maximum of 1 or 2 base mismatches. In some embodiments, the two sequences may be at least 80%, 85%, 90%, or 100% complementary. In other embodiments, the library may comprise at least 30%, at least 50%, at least 80%, at least 85%, at least 90%, or at least 95% of all possible sequences having a certain length or lengths.

In certain embodiments, a nucleic acid probe may comprise at least one residue that can enhance residue stacking and/or backbone pre-organization. This can significantly increase the thermal stability (melting temperature) of the nucleic acid probe in some cases. For example, a nucleic acid probe may comprise at least one locked nucleic acid (LNA) residue. A locked nucleic acid residue is a nucleic acid analog that has a chemical shape similar to a naturally occuring nucleic acid residue (e.g., being able to form 2 or 3 hydrogen bonds with a complementary residue), but is not free to rotate in as many dimensions as a naturally occuring nucleic acid residue. For instance, in some cases, a locked nucleic acid residue may contain a 2'-O, 4'-C methylene bridge, where the methylene bridge "locks" the ribose in the 3'-endo structural conformation, which is often found in the certain form of DNA or RNA. In some cases, the locked ribose conformation may significantly increase the thermal stability of the nucleic acid probe. Other residues that can increase the thermal stability of a nucleic acid sequence will be apparent to those skilled in the art. For example, peptide nucleic acids may be used as nucleic acid probes in some cases.

In certain embodiments, the nucleic acid probe can contain a universal residue, which may be able to engage in a residue-pairing relationship with more than one natural nucleotide, and in some cases, with all of the natural nucleotides. A universal base or universal residue (e.g., "N"), as used herein, refers to a base that, when incorporated into a polymeric structure in the form of a nucleobase (e.g., a nucleotide or a PNA) does not significantly discriminate between bases on a complementary polymeric structure having nucleobases. For example, a universal base can hybridize to more than one nucleotide selected from A, T, C, and G. Universal residues will be known to those or ordinary skill in the art. Non-limiting examples of universal residues include deoxyinosine, 3-nitropyrrole, 4-nitroindole, 6-nitroindole, 5-nitroindole, 6-methyl-7-azaindole, pyrrollpyrizine, imidizopyridine, isocarbostyril, propynyl-7-azaindole, propynylisocarbostyril, allenyl-7-azaindole, 8-aza-7-deaza-2'-deoxyguanosine, 8-aza-7-deaza-2'-deoxyadenosine, 2'-deoxycytidine, 2'-deoxyuridine, 2'-deoxyadenosine, 2'-deoxyguanosine, 7-deaza-2'-deoxyinosine, 2'-aza-2'-deoxyinosine, 3'-nitroazole, 4'-nitroindole, 5'-nitroindole, 6'-nitroindole, 4-nitrobenzimidazole, nitroindazole (e.g., 5'-nitroindazole), 4-aminobenzimidazole, imidazo-4,5-dicarboxamide, 3'-nitroimidazole, imidazole-4-carboxamide, 3-(4-nitroazol-1-yl)-1,2-propanediol, and 8-aza-7-deazaadenine. Other universal residues useful for the systems and methods described herein will be known to those of skill in the art.

The nucleic acid probes may be fastened to particles (e.g., microparticles, beads, etc.), for example, such that some or all of the particles each contain only one type of nucleic acid probe (which may include many identical copies of that probe). Techniques for fastening a nucleic acid to a particle are known in the art and include, for example, forming an ester bond between the 3' hydroxyl group of the nucleic acid and a linker attached to a particle. The linker may be any suitable linker. For example, the linker may be of sufficient length to allow a nucleic acid probe to hybridize to a target nucleic acid. Additionally, the linker may be of sufficient length such that at least two nucleic acid probes can hybridize to a target nucleic acid. In addition, materials and methods for attaching a nucleic acid to a particle are available commercially from a variety of sources, such as Luminex Corp. which sells xMAP® COOH Development Microspheres.

The particle may be any solid entity that can be dispersed in a fluid. The particles may be prepared such that some or all of the particles each have only one nucleic acid probe sequence fastened to the particle, although multiple copies of the nucleic acid probe may be fastened to the particle. In other embodiments, however, more than one nucleic acid probe sequence may be present in the nucleic acid probes fastened to a given particle. In addition, in some cases, different particles may independently have the same or different nucleic acid probe sequence (e.g., such that there is some redundancy so that not each particle in a given population or collection of particles is necessarily unique).

The particles may have any dimension and may be spherical or non-spherical. For instance, the particles may have average diameters ranging from approximately 100 nm to 100 microns in diameter in some cases. In certain embodiments, the particles may have an average diameter of less than about 10 microns, less than about 1 micron, less than about 300 nm, less than about 100 nm, less than about 30 nm, less than about 10 nm, or less than about 5 nm. The average diameter, as used herein, is the arithmetic average of the diameters of the particles. The diameter of a non-spherical particle, as used herein, is the diameter of a perfect mathematical sphere having the same volume as the particle.

The particle may comprise any suitable material to which nucleic acid probes can be immobilized. In some instances, the particle may be polymeric. Examples of polymeric materials include non-degradable materials such as polystyrene and degradable materials such as polylactide. In other embodiments, the particle may comprise an inorganic material. For instance, the particle may be a quantum dot such as cadmium selenide, a metal such as gold, a ceramic such as glass, etc. In other cases, the particle may be gel, for example a hydrogel (e.g. agarose, polyacrylamide, etc.).

In some embodiments, a particle may be solid, i.e. a continuous material or mixture of materials. In other embodiments, the particle may have a core-shell structure where, for example, the core comprise one material and the shell comprises a second material. The core may be a solid, a liquid, a gel, or mixtures thereof. In still other embodiments, the particle may be hollow.

In some embodiments, at least one identification entity is associated with a particle (and in some cases, the particle itself acts as the identification entity). An "identification entity" as used herein, is a species that is or includes a component that can be determined in some fashion. For example, the identification entity may be identified when contained within a particle or bound to the surface of the particle. Non-limiting examples include identification entities detectable by fluorescence, chemiluminescence, radioactivity, or the like. Specific examples include, but are not limited to, fluorescent molecules or particles, dyes, radioisotopes, quantum dots, etc. In some cases, the identification entities can be used to distinguish between different particles, e.g., different particles containing different nucleic acid probes.

Identification entities may be distinguished using any suitable method, e.g., color, fluorscence, absorption, intensity, size, charge, radioactivity, mass, or the like. One non-limiting example of a plurality of distinguishable identification entities are the Luminex FlexMAP Microsphere particles commercially available from Luminex Corp. Beads or particles such as these may be distinguished, according to one embodiment, by the use of two or more dyes or other compounds that can be independently varied within each bead or particle. Therefore, a plurality of distinguishable particles may be used as a plurality of identification entities, according to certain embodiments. As another, specific non-limiting example, particles comprising polystyrene and one or more dyes may be used as identification entities. The dyes employed within the particles may include, for instance, squaric acid-based molecules or other fluorescent molecules that exhibit fluorescence, e.g., extending into near infrared and/or infrared region. In some cases, two or more dyes with concentrations that can be independently controlled can be used within each particle. In certain embodiments, a plurality of identification elements associated with a plurality of particles may be encapsulated in a single larger particle. For example, a plurality of approximately 1 micron particles can be encapsulated in a 10 micron gel particle. The larger particle may have nucleic acid probes fastened to the surface.

Thus, for example, in one set of embodiments, the surface of a first particle may have fastened thereto a plurality of nucleic acid probes of a first sequence (i.e., essentially all of the nucleic acid probes fastened to the first particle have identical sequences), the surface of a second particle may have fastened thereto a plurality of nucleic acid probes of a second sequence (i.e., essentially all of the nucleic acid probes fastened to the second particle have identical sequences), etc.

Another set of embodiments for sequencing a target nucleic acid uses ligases to join nucleic acid probes together in the presence of a target nucleic acid. An example is as follows. A particle may be provided that comprises at least a first and a second nucleic acid probe selected from a first group and a second group of nucleic acid probes, respectively. The nucleic acid probes each comprise a sequence of nucleic acid residues attached to a signaling entity, as discussed more herein. The particle can be contacted with a target nucleic acid using any suitable method, as discussed herein. The nucleic acids can be exposed to a ligase which can ligate the first and second nucleic acids together if the complementary sequence is found on the target nucleic acid. The ligase can be incorporated in a fluidic droplet containing the target nucleic acid and the particle, or simply in a solution such that it can interact with the particle and nucleic acid. Thus, if the first and second nucleic acid probes are able to bind to the target nucleic acid, the probes will be ligated together, and this ligation can be detected. As discussed herein, by identifying which probes exhibit ligation, the sequence of the target nucleic acid (or at least a portion thereof) may be determined, e.g., using SBH or similar techniques, such as those discussed below.

Figure 5A:
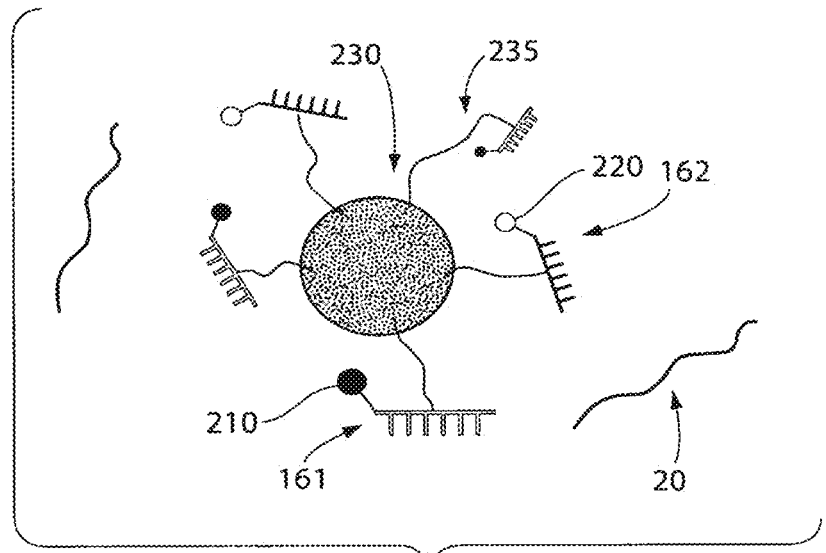
FIG. 5A shows a particle with nucleic acid probes fastened thereto according to still another embodiment of the invention.
Figure 5B:
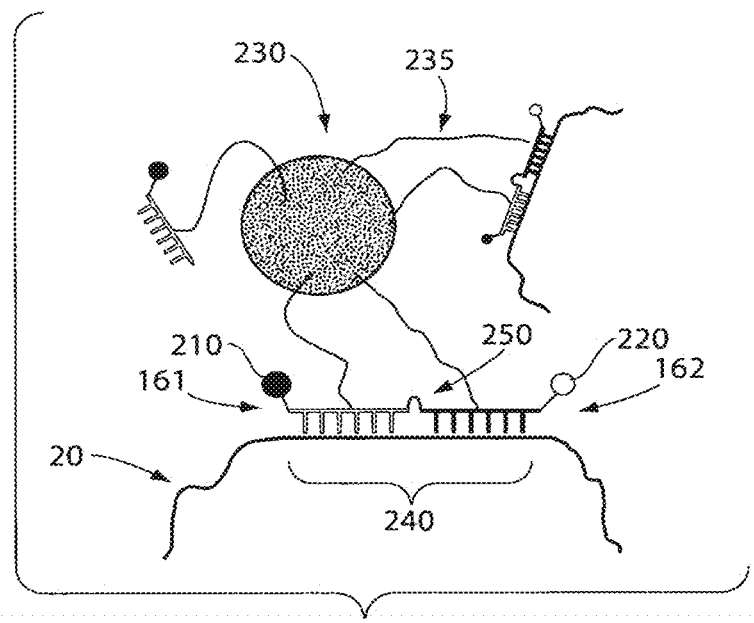
FIG. 5B shows hybridization of two nucleic acid probes to a target nucleic acid according to still another embodiment of the invention.

A non-limiting example of a ligation method of the present invention is illustrated in FIG. 5. As shown in FIG. 5A, target nucleic acid 20 is exposed to a first nucleic acid probe 161 comprising a first signaling entity 210 and a second nucleic acid probe 162 comprising a second signaling entity 220 attached to a particle 230 through a linker 235. In some cases, the first and second nucleic acid probes may hybridize with the target nucleic acid adjacent to each other as shown in FIG. 5B, and as indicated by 240. Target nucleic acid 20 comprising the first 161 and second 162 nucleic acid probes may then be exposed to a ligase and ligated together to form a nucleic acid oligomer. In some cases, however, the first and the second nucleic acid probes do not hybridize adjacent to each other on the target nucleic acid. In such instances, upon exposure of the target nucleic acid comprising the first and second nucleic acid probes to a ligase, no substantial ligation of the nucleic acid probes will occur. In some cases, one or both of the nucleic acid probes will not hybridize to the target nucleic acid (e.g., the sequence is not substantially complimentary), and no ligation will occur between the first nucleic acid probe and the second nucleic acid probe.

In some embodiments, the first and the second nucleic acid probes can associate with the target nucleic acid, e.g., if the target nucleic acid and the nucleic acid probes have substantial complementarity. In these instances, the nucleic acid probes may be joined together (e.g., via ligation with the ligase), which can be used (as discussed herein) to determine the association with the nucleic acid probe. For instance, in some cases, the first nucleic acid probe and the second nucleic acid probe will associate (e.g., hybridize) with the target nucleic acid in positions adjacent to each other (e.g., the sequence of the first nucleic acid is substantially complimentary with the target nucleic acid and the sequence of the second nucleic acid is substantially complimentary with the target nucleic acid adjacent to the sequence which is substantially complimentary with the first nucleic acid probe). In such cases, ligation of the first and the second nucleic acid probes can occur due to the presence of the ligase. However, in other instances where the first and the second nucleic acid probes do not associate in positions adjacent on the target nucleic acid, no ligation can occur. As an example, the first and the second nucleic acid may have sequences which are substantially complimentary with the target nucleic acid but the sequences are not adjacent to each other (e.g., one or more residues may be present in the target nucleic acid probe between the sequence complimentary to the first and the second nucleic acid probes).

In some embodiments, it may be advantageous to use ligation methods such as described above for sequencing a target nucleic acid. For example, as described more herein, such methods may allow the formation of relatively large sequencing libraries from smaller libraries. This can reduce and time to and/or cost of the (e.g., cost of reagents) synthesis of the library. In addition, the ligation method can comprise enhanced signals, in some embodiments, as compared to non-ligation methods, since ligation increases probe length, which in turn can increase the binding energy. In some cases, such methods may increase single base pair specificity, thereby increasing the accuracy of the sequencing process. This is because shorter nucleic acid probes may have higher single-base pair specificity as compared to a longer nucleic acid probes. Specificity and binding energy may also be enhanced in some cases by using nucleic acid probes comprising universal bases, locked-nucleic acids, gaps, or other biochemical reagents to engineer probe structure and optimize the process, e.g., as discussed herein. The ligation method may also advantageously combine the benefits of using a library comprising both long and short nucleic acid probes in some cases. For example, short probes may be used to form longer probes, which generally will be more tightly bound to the nucleic acid probe. On the other hand, longer probes are generally less specific than shorter nucleic acid probes due to flexibility of the probe. Therefore, certain ligation methods may take advantage of some of the benefits of shorter or longer probes (e.g., specific binding of shorter probes, but once bound, the shorter probes are ligated to form a longer probe, therefore the binding is tighter).

In some cases, the first group of nucleic acid probes and/or the second group of nucleic acid probe may comprise at least a portion of all of the sequences of a selected length, or a subset thereof. For example, the first group of nucleic acid probes may comprise at least one of each of a portion of all probes with 3 nucleic acid residues (optionally further containing universal residues), as discussed herein. The first group of nucleic acid probes and the second group of nucleic acid probes may or may not be substantially similar. In some cases, the first group of nucleic acid probes comprise substantially the same probes as the second group of nucleic acid probes. In some cases, the first group and the second group of nucleic acid probes comprises all possible sequences of a particular length, e.g., 3-mers, 4-mers, 5-mers, 6-mers, 7-mers, 8-mers, 9-mers, 10-mers, or the like.

The first group and the second group of nucleic acid probes may be substantially similar or different. For example, the first group and the second group of nucleic acids may be substantially similar if the first group and the second group comprises at least a portion of all possible 3-mers, but may differ in that they comprise differing signaling entities or the signaling entity is located at differing positions (e.g., 3'-end vs. 5'-end). The first group of distinguishable identification elements and the second group of distinguishable identification elements may be the substantially similar or different.

Other nucleic acid residues may also be present in some cases, in addition to A, G, C, and T. For instance, in some cases, at least some of the nucleic acid probes may additionally comprise at least one universal residue. For example, a 3-mer comprising additional universal residues may have the sequence UUUXXX wherein U is a universal residue and XXX is either one of A, G, C, or T (e.g., the 3-mer). Thus, as a non-limiting example, two 6-mer sequences may be ligated together, where each of the 6-mer sequences contains three naturally-occurring residues and three universal residues; thus, there will be $4^3$ possible first nucleic acid probes and $4^3$ possible second nucleic acid probes that can be ligated together, and identification of the ligation between the first and second nucleic acid probes can be used to identify a sequence of 6 nucleic acids, even though each of the first and second nucleic acid probes binds to the target nucleic acid with the affinity of a 6-mer, not a 3-mer, due to the presence of the three universal residues.

In some cases, the first group of nucleic acid probes may be capable of ligating only on the 3' end of the nucleic acid probe and the second group of nucleic acid probes may be capable of ligating on the 5' end, such the only one end of each of the first nucleic acid probe and the second nucleic acid probe may ligate with each other. Therefore, the probes need to hybridize to the target nucleic acid in the correct order in order for ligation to occur. That is, the probes must hybridize to the target nucleic acid such that the 3' end of the first probe and the 5' end of the second probe are adjacent to each other and the probes are capable of being ligated. If the first probe and the second probe hybridized to the target nucleic acid such that the 5' end of the first probe and the 3' end of the second probe are adjacent to each other, the probes may not be capable of binding (e.g., if the 5' end of the first probe and the 3' end of the second probe comprise an entity (e.g., signaling entity, etc.) that prevents hybridization at that end).

The ligation of the first and the second nucleic acid probes may be determined, for example, by a change in a signaling entity associated with at least one of the nucleic acid probes. If the first and the second nucleic acid probes are complementary or substantially complementary in adjacent positions to the target nucleic acid, then the first and the second nucleic acid probes (including a signaling entity) associates with the target nucleic acid and participate in a ligation reaction as discussed above. Accordingly, by determining the signaling entity of the ligated nucleic acid probes, a portion of the sequence of the target nucleic acid may be determined, based on both the sequences of the nucleic acid probes. Conversely, if the first or the second nucleic acid probes are not able to associate with the target nucleic acid sequence (e.g., if the sequences are not sufficiently complementary), then no ligation reaction can occur, and the determined signal entity will have a different signal. In some cases, each nucleic acid probe from the first group comprises a first signaling entity 210 and each nucleic acid probe from the second group comprises a second signaling entity 220, as shown in FIGS. 5A and 5B. The ligation of a first and a second nucleic acid probe may be determined by determining the first and/or second signaling entity. For example, a particle may have fastened to the surface a first nucleic acid probe 161 containing a first signaling entity 210 and a second nucleic probe 162 containing a second signaling entity 220, the sequence of the first nucleic acid probe being different from the sequence of the second nucleic acid probe.

Figure 6:
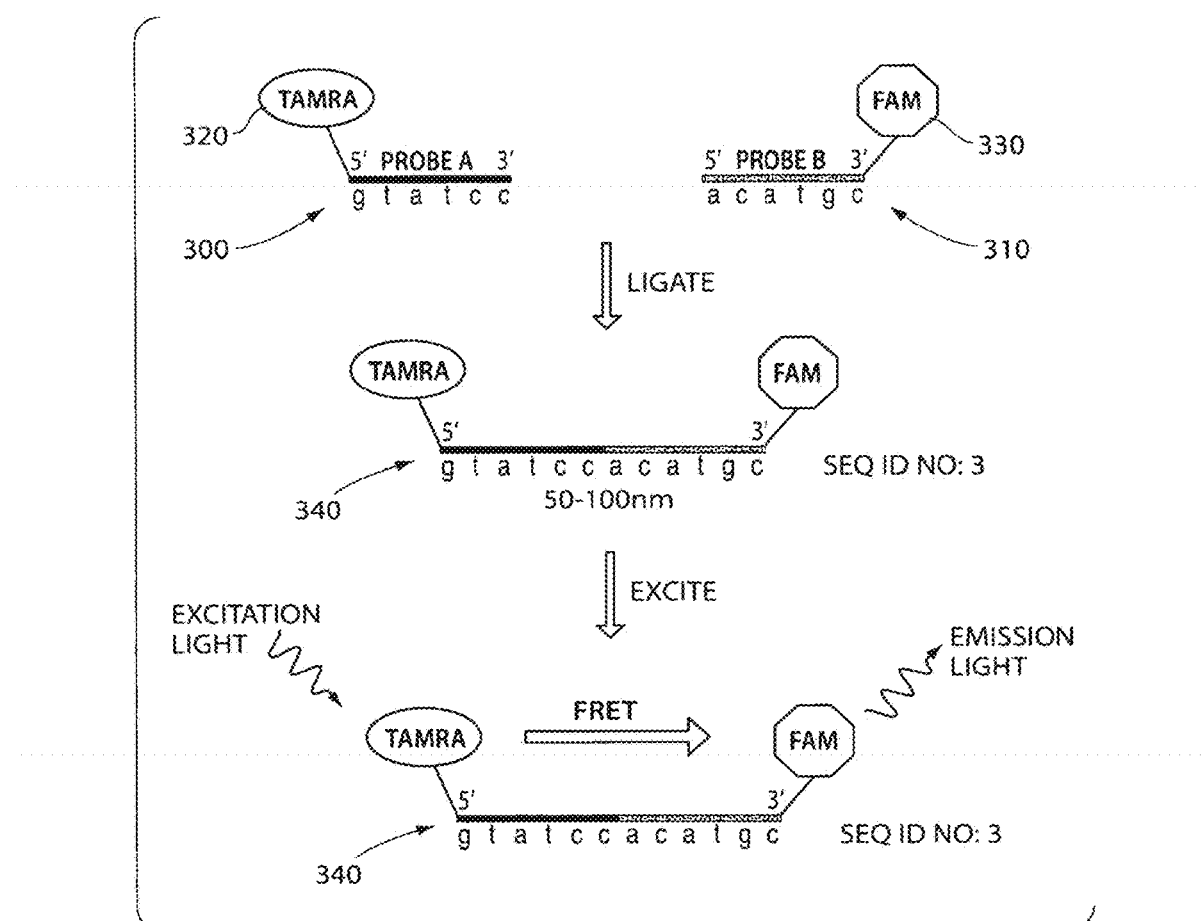
FIG. 6 shows interaction between two signaling entities according to still another embodiment of the invention.

In some cases, the first and second signaling entities may interact in a determinable manner if placed within a suitable distance from each other. For example, a signaling entity may be a quencher or enhancer. The quencher or enhancer may be any entity able to affect the signaling entity in some fashion, e.g., by respectively inhibiting or facilitating determination of the signaling entity. For instance, the proximity of a fluorescent signaling entity and a quencher within a nucleic acid probe may be such that the quencher is able to partially or completely inhibit fluoresence of the signaling entity, while an enhancer may be able to enhance the fluorescence of a fluorescent signaling entity when the enhancer is positioned proximate the signaling entity. The quencher or enhancer may also be located anywhere in the nucleic acid probe, for example, attached to the 3' end of the nucleic acid sequence. Non-limiting examples of quenchers include tetramethylrhodamine and dihydrocyclopyrroloindole tripeptide. In another, non-limiting example, a first and second signaling entities may be two different fluorescent molecules that can produce a FRET signal if placed within a suitable distance from each other. For example, the two signaling entities may be TAMRA (tetramethyl-6-carboxyrhodamine) and FAM (6-carboxyfluorescein), as shown in FIG. 6, which illustrates one example. Provided are a first nucleic acid probe 300 having a TAMRA signaling entity 320 attached and a second nucleic acid probe 310 having a FAM signaling entity 330 attached. Nucleic acid probes 300 and 310 bind to a target nucleic acid (not shown) as described elsewhere herein adjacent to each other and are ligated (e.g., using ligase) together to form a single oligonucleotide 340. Excitation of TAMRA with a suitable light source (e.g., 488 nm light) produces FRET and a corresponding emission of light from FAM (e.g., 580 nm light), which can be detected.

As a non-limiting example, a quencher (or similarly, an enhancer) can be used within a signaling entity in a nucleic acid probe as follows. A nucleic acid probe associated with a target nucleic acid may be removed or dissociated from the target nucleic acid by the action of certain enzymes or other species, for instance, polymerases such as Taq polymerases. For instance, in some cases, a polymerase may cause degradation of the nucleic acid sequence within the nucleic acid probe to occur, which may cause release of the signaling entity and/or the quencher or enchancer and hence, the quencher or enhancer may no longer be proximate to or at least substantially affect the signaling entity. Thus, degradation of the nucleic acid probe can be determined by determining a change in the signaling entity. In contrast, in systems where the nucleic acid probe does not sufficiently associate with the target nucleic acid (e.g., if no sufficiently complementary sequences are present), no degradation of the nucleic acid probe would occur through action of the polymerase or other species (e.g., any association that exists between the target nucleic acid and the nucleic acid probe is too transient or short for enzymatic action to occur), and thus, no significant change in the signal of the signaling entity could be determined. Accordingly, in one embodiment, a polymerase such as Taq polymerase may be provided to a fluidic droplet comprising a nucleic acid probe and a target nucleic acid. The polymerase may be provided to the fluidic droplet using any suitable technique, as discussed herein.

As a non-limiting example, if two 3-mer nucleic acid probes are complimentary, hybridize adjacently, and in the correct order, they may be ligated, forming a new 6-mer (3-mers are used as an illustrative example; other lengths may also be used in some cases, e.g. 4-mers, 5-mers, 6-mers, 7-mers, or the like). Ligation covalently bonds together the two 3-mer probes forming a more tightly bound 6-mer. Before ligation, the binding energies of the probes are merely that of the 3-mers, which is generally too small to be detected at room temperature. After ligation, the two 3-mers become a 6-mer, and thus can hybridize. Ligation of the probes thus relies on the highly specific but transient binding of the short probes to produce a tightly bound combined probe.

In some cases, however, a 3-mer nucleic acid probe may be simulated using a longer nucleic acid probe containing one or more universal residues. For example, a 3-mer comprising additional universal residues may have the sequence UUUXXX wherein U is a universal residue and XXX is either one of A, G, C, or T (e.g., the 3-mer). The nucleic acid probe acts as a 3-mer in that it recognizes any nucleic acid having a sequence complementary to the XXX portion of the nucleic acid probe, as the UUU portion of the nucleic acid probe will bind to any sequence. Accordingly, such a nucleic acid probe may act as a 3-mer nucleic acid probe (i.e., having the specificity of a 3-mer probe), although it may exhibit the binding affinity of a 6-mer sequence. Thus, in any descriptions herein of 3-mer nucleic acid probes, the actual length of the nucleic acid probe may be longer due to the presence of universal residues, which may be present at any location within the nucleic acid probe.

In some cases, the nucleic acid probes may be used to form a library of nucleic acid probes. The library may include a plurality of such nucleic acid probe sequences, for example, organized by attachment to particles. Thus, for example, a library may comprise a plurality of particles, the particles being identifiable (e.g., using identification entities) and having unique nucleic acid probes on each of the particles such that each particle contains only one type of nucleic acid probe, but many identical copies of that probe.

In some (but not all) embodiments, the library may contain sequences that have roughly the same number of residues, for example, around 4 residues, around 5 residues, around 6 residues, around 7 residues, etc. The library of nucleic acid probes may be prepared using any suitable technique, and may be produced using manual techniques or automated, e.g., using a robotic apparatus.

A library of nucleic acid probes having varying sequences may be selected such that at least some of the probes will contain sequences complementary or substantially complementary to the target nucleic acid sequence. For instance, in one embodiment, the nucleic acid probe sequences are selected such that every permutation of nucleic acid residues of a certain size or number (or range of sizes or numbers) is represented, thereby ensuring that at least one of those nucleic acid probe sequences is substantially complementary to the target nucleic acid. For example, for a nucleic acid probe having a sequence n bases in length, the number of sequence permutations in a complete library equals $4^n$ (n=1, 2, 3, 4, 5, 6, 7, 8, etc.). Thus, when n=4, there would be 256 unique nucleic acid probes; when n=5, there would be 1,024 unique nucleic acid probes; when n=6, there would be 4,096 unique nucleic acid probes; when n=7, there would be 16,384 unique nucleic acid probes; when n=8, there would be 65,536 unique nucleic acid probes; etc.

Thus, in one embodiment, a probe library may be prepared that comprises a collection of particles, some or all of which contain an identification entity and a plurality of nucleic acid probes fastened to the surface of the particles. For example, in one embodiment, a probe library can be prepared that includes a collection of fluorescent particles, each of which can be identified by an identification entity associated with each particle, and each of which has a plurality of nucleic acid probes having essentially identical sequences fastened to the surface of each respective particle. The identification entity of a particle is associated with a unique nucleic acid probe sequence in some cases. For example, a first particle may be distinguished from a second particle using a first identification entity associated with the first particle and a second identification entity associated with the second particle, where the first and second identification entities are distinguishable in some fashion. In some cases the plurality of particles contains at least one unique nucleic acid probe, at least 2 unique nucleic acid probes, at least 5 unique nucleic acid probes, at least 10 unique nucleic acid probes, at least 50 unique nucleic acid probes, least 100 unique nucleic acid probes, at least 120 unique nucleic acid probes, at least 200 unique nucleic acid probes, at least 500 unique nucleic acid probes, at least 1,000 unique nucleic acid probes, at least 4,000 unique nucleic acid probes, at least 16,000 unique nucleic acid probes, at least 65,000 unique nucleic acid probes, etc. In some instances, the plurality of particles contains at least 101 unique nucleic acid probes. In some embodiments, the nucleic acid probes may contain 4-mer nucleic acid probes, 5-mer nucleic acid probes, 6-mer nucleic acid probes, etc. Modifications such as including LNAs, universal bases, gaps, and random sequences in the nucleic acid probes may be used, as described in more detail herein, to optimize the nucleic acid probes. Additionally, some or all of the nucleic acid probes may have at least one signaling entity attached thereto.

As discussed, the sequence of a target nucleic acid may be determined by determining the association (or the non-association) of the target nucleic acid to one of a plurality of distinguishable particles having attached nucleic acid probes. The target nucleic acid may be bound to the nucleic acid probe when they form a relatively stable duplex by hydrogen bonding under experimental conditions. Relatively stable hydrogen bonding may be formed due to Watson-Crick complementarity (e.g., A matches T, but not G or C G matches C, but not A or T) and/or other effects such as GC wobble, or other associations caused by locked nucleic acids or universal bases, as discussed herein. Non-limiting examples of suitable methods for determining the sequence of a target nucleic acid include sequencing by hybridization techniques that are known to those of ordinary skill in the art.

As discussed, the sequence of the target nucleic acid may be determined, based on binding of the particles, using sequencing by hybridization (SBH) algorithms or other known techniques. For example, once particles binding the target nucleic acid have been identified, the nucleic acid probes associated with each of the binding particles can also be identified, and the sequences of these nucleic acid probes (or their complements) can then be used to reconstruct the sequence of the target nucleic acid, using techniques known to those of ordinary skill in the art, such as sequencing by hybridization.

Sequencing by hybridization (SBH) is a method for examining the nucleic acid residue sequence in a target nucleic acid that has been previously described, for instance, in U.S. Pat. No. 5,202,231, incorporated herein by reference, and other references known to those of ordinary skill in the art. In general, SBH uses a set of nucleic acid probes of defined sequence to probe for complementary sequences on a longer target strand of a target nucleic acid. The defined sequences which hybridize to the target can then be aligned using computer algorithms to construct the sequence of the target nucleic acid.

Thus, in one embodiment of the present invention, a target nucleic acid may associate with a certain set of nucleic acid probes fastened to particles, leading to a characteristic "hybridization" pattern. Each positive association (or hybridization) event in a given sample provides information about the target nucleic acid. In some cases the target nucleic acid may be sequenced without determination of exactly where any particular nucleic acid probe associates with the target nucleic acid. Algorithms and software have been developed for target nucleic acid reconstruction, based on the hybridization pattern, and are known to those skilled in the art. In other cases, however, analysis of a hybridization pattern, such as those described herein, may provide a "fingerprint" labeling of the target nucleic acid sequence, without specifically determining the target nucleic acid sequence itself. The pattern of hybridization may also be manually or computer analyzed.

Any suitable determination method can be used to determine the identification entities and/or the signaling entities, depending on the application. As mentioned, the determination may occur using techniques such as radioactivity, fluorescence, phosphorescence, light scattering, light absorption, fluorescence polarization, or the like. Many detectors that operate using such principles are commercially available. The detector may be used to determine at least one of the signaling entities and/or identification entities that may be present, and in some cases, more than one detector may be used.

In some embodiments, the particles flow past a detector single file. For example, in certain cases where the particles are contained within a droplet, as discussed below, the droplet may be deformed such that the particles contained within the droplet pass the detector single file. A droplet may be deformed by passing it through a channel that has a constriction such that the cross-sectional area of the constriction is smaller than the cross-sectional area of the droplet when the droplet is in free solution. In some cases, the droplet is deformed such that substantially all of the signaling entities and/or identification entities are arranged single file within the droplet. For instance, the signaling entities and/or identification entities may be arranged within a channel such that no line drawn from a first wall of the channel, normal to the first wall, to a second wall of the channel intersects more than one particle.

In some embodiments, the detection may be parallelized, i.e., a number of signaling entities and/or identification entities may be simultaneously determined within one channel and/or within a plurality of channels. For example, a timing device may be used to synchronize detection of the parallel paths. Another non-limiting example of parallelized detection is the use of a camera positioned so as to be able to image more than one channel, e.g., simultaneously. The camera may be, for example, a linescan camera, a 2D CCD camera, or the like. Additional devices and methods suitable for use in the present invention can be found in U.S. application Ser. No. 61/008,862 entitled "Systems and Methods for Nucleic Acid Sequencing," filed Dec. 21, 2007, and U.S. application Ser. No. 61/098,710 entitled "Systems and Methods for Nucleic Acid Sequencing," filed Sep. 19, 2008, which are incorporated herein by reference in their entirety. In one specific embodiment, at least one mercury arc lamp may illuminate a selected number of channels and multiple cameras (which may each have an individual filter) may be used to capture a particular color spectrum. The images may be captured sequentially, or simultaneously, e.g., so that the location of each droplet is the same in all camera images.

Thus, in certain instances, a plurality of particles may be determined at a single time. In some cases, in order to simultaneously image an array of particles, the detector may need to determine the boundaries of adjacent particles such that only one signal is determined per particle. According to one set of embodiments, the following methods and/or systems employing a light source to create particle glare may be advantageous when determining a plurality of particles which are collected in a contained area.

In some cases, particles may be determined by determining a signal of a position relative to a reference spot. That is, each particle may be related to a references spot and a determination of the signal of a particle may be determined by relation to the reference spot. Production of a reference spot may be accomplished, for example, by shining a light on the surface of the particles such that glare is produced for each particle. This may allow for the detector to determine a relative location for each particle, and thereby determine a signal each particle, as described more herein.

In some cases, when determining a plurality of particles, a second light source (e.g., a lamp, an LED array), in addition to the light source used to probe for fluorescence may be employed. The second light source may be shone at an angle (e.g., a non-orthogonal angle) to the particles being determined (e.g., being visualized under a microscope). Due to the orientation of the light and the spherical shape of the particles, scattered light may be captured by the lens of the camera and a relatively concentrated and bright glare on the image of each particle is produce (e.g., a particle glare) that is easily visible and distinguishable from the background signal. Thus, a substantially focused glare may be produced by the particle due to the scattering of light within the particle.

Images of the plurality of particles may be captured by a detector or an imager, such as a CCD camera. In some embodiments, the CCD cameras may comprise filters that only allow for light in a narrow spectrum to pass to the camera (e.g., red light, green light, etc.) such that specified fluorescent images may be obtained. In instances where more than one camera is employed, the capture of images may or may not be synchronized. In some embodiments, e.g., if the particle glare formed is distinctly more intense than the background, software identification of the location of the particles may be completed using simple methods. The particle glare can be used as a reference point as the particle glare generally appears consistently in regards to both direction and distance from the center of each particle. Depending on the set-up of the oblique lighting, the particle glares can be placed offset from the center of the particle and allowing for the same image frame for both particle identification and data acquisition.

In some cases, at least one image (e.g., comprising the particle glares) may be processed by using a simple intensity threshold programs to determine the particle glares on each particle. The software can compute, or human input may be used, to determine the angle and/or the distance between a particle glare and the center of the particle. In some embodiments, the angle and/or distance between a particle glare and the center of the particle may be recorded a single time.

In some cases, the techniques discussed herein can be used to sequence relatively long nucleic acids. For example, many smaller target nucleic acid sequences may be determined, and the sequences can be assembled to reveal the complete sequence for the original larger target nucleic acid. Such techniques may be useful for sequencing the genome of an organism, for example. For example, in one set of embodiments, a large target nucleic acid (e.g., a gene, chromosome, genome, etc.) may be dissociated into smaller target nucleic acids. In one example, the 3 billion base-pair human genome target may be broken into approximately 1000 base-pair target nucleic acids using a variety of techniques known in the art (e.g. sonication). The target nucleic acids may be injected into a microfluidic device or other system where they can be sequenced, as discussed above. In some instances, a target nucleic acid can be encapsulated in a fluidic droplet. A target nucleic acid in a droplet can be amplified using a technique such as PCR and labeled using techniques described herein. The resulting emulsion comprises a collection of droplets, and at least some of the droplets may contain many copies of a unique target nucleic acid sequence.

As mentioned, various embodiments of the invention are directed towards containing nucleic acids and/or other species within fluidic droplets. As used herein, a "fluid" is given its ordinary meaning, i.e., a substance that tends to flow and to conform to the outline of its container. Typically, fluids are materials that are unable to withstand a static shear stress, and when a shear stress is applied, the fluid experiences a continuing and permanent distortion. Thus, the fluid may have, in some cases, any suitable viscosity that permits at least some flow of the fluid. Non-limiting examples of fluids include liquids and gases, but may also include free-flowing solid particles, viscoelastic fluids, and the like.

A "droplet," as used herein, is an isolated portion of a first fluid that is completely surrounded by a second fluid. It is to be noted that a droplet is not necessarily spherical, but may assume other shapes as well, for example, depending on the external environment. In one embodiment, the droplet has a minimum cross-sectional dimension that is substantially equal to the largest dimension of the channel perpendicular to fluid flow in which the droplet is located. The diameter of a droplet, in a non-spherical droplet, is the diameter of a perfect mathematical sphere having the same volume as the non-spherical droplet. The fluidic droplets may be created using any suitable technique, such as those disclosed in U.S. patent application Ser. No. 11/024,228, filed Dec. 28, 2004, entitled "Method and Apparatus for Fluid Dispersion," by Stone, et al., published as U.S. Patent Application Publication No. 2005/0172476 on Aug. 11, 2005 now U.S. Pat. No. 7,708,949, issued May 4, 2010; U.S. patent application Ser. No. 14/246,911, filed Oct. 7, 2005, entitled "Formation and Control of Fluidic Species," by Link, et al., published as U.S. Patent Application Publication No. 2006/0163385 on Jul. 27, 2006, now U.S. Pat. No. 9,038,919, issued May 26, 2015; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, now U.S. Pat. No. 8,765,485, issued Jul. 1, 2014 each incorporated herein by reference.

Various embodiments of the invention use a plurality or series of fluidic droplets. The fluidic droplets may be polydisperse (e.g., having a range of different sizes), or in some cases, the fluidic droplets may be monodisperse or substantially monodisperse, e.g., having a homogenous distribution of diameters, for instance, such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter. The "average diameter" of a population of droplets, as used herein, is the arithmetic average of the diameters of the droplets. Those of ordinary skill in the art will be able to determine the average diameter of a population of droplets, for example, using laser light scattering or other known techniques. As non-limiting examples, the average diameter of a droplet may be less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers. The average diameter of the droplet may also be at least about 1 micrometer, at least about 2 micrometers, at least about 3 micrometers, at least about 5 micrometers, at least about 10 micrometers, at least about 15 micrometers, or at least about 20 micrometers in certain cases.

In one embodiment, droplets containing the nucleic acids can be produced in parallel. For instance, a microfluidic device may be used to allow for parallel creation of a library of droplets containing target nucleic acids. For instance, a microfluidic drop maker may be replicated many times on a single chip, and each drop maker may be used to droplets containing target nucleic acids. Non-limiting examples of techniques of producing droplets of fluid surrounded by a liquid are described in U.S. patent application Ser. No. 11/024,228, filed Dec. 28, 2004, entitled "Method and Apparatus for Fluid Dispersion," published as U.S. Patent Application Publication No. 2005/0172476 on Aug. 11, 2005, now U.S. Pat. No. 7,708,949, issued May 4, 2010; U.S. patent application Ser. No. 14/360,845, filed Feb. 23, 2006, entitled "Electronic Control of Fluidic Species," published as U.S. Patent Application Publication No. 2007/000342 on Jan. 4, 2007 now U.S. Pat. No. 8,765,485, issued Jul. 1, 2014; or U.S. patent application Ser. No. 11/368,263, filed Mar. 3, 2006, entitled "Systems and Methods of Forming Particles," published as U.S. Patent Application Publication No. 2007/0054119 on Mar. 8, 2007 (now abandoned), each incorporated herein by reference. For example, in some embodiments, an electric charge may be created on a fluid surrounded by a liquid, which may cause the fluid to separate into individual droplets within the liquid.

In some, but not all embodiments, all components of the systems and methods described herein are microfluidic. "Microfluidic," as used herein, refers to a device, apparatus or system including at least one fluid channel having a cross-sectional dimension of less than 1 mm, and a ratio of length to largest cross-sectional dimension perpendicular to the channel of at least 3:1. A "microfluidic channel," as used herein, is a channel meeting these criteria.

Microfluidic systems may be provided that are able to cause two or more droplets to fuse or coalesce into one droplet, for example, in cases where the two or more droplets ordinarily are unable to fuse or coalesce, for example due to composition, surface tension, droplet size, etc. as known to those of ordinary skill in the art. The fluidic droplets may be fused together using any suitable technique, for example, as discussed in U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006, now U.S. Pat. No. 9,038,919, issued May 26, 201.5; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, now U.S. Pat. No. 8,765,485, issued Jul. 1, 2014, each incorporated herein by reference. As an example, in microfluidic systems, the surface tension of the droplets, relative to the size of the droplets may prevent fusion or coalescence of the droplets from occurring. In one embodiment, two droplets may be given opposite electrical charges (i.e., positive and negative charges, not necessarily of the same magnitude), which may increase the electrical interaction of the two droplets such that fusion or coalescence of the droplets can occur. Electrical charges (positive or negative) may be imparted onto droplets through the use of Taylor cones, or through any other suitable techniques. For instance, an electric field may be imposed on a reactor containing the droplets, the droplets may be passed through a capacitor, a chemical reaction may occur to cause the droplets to become charged, flowing the droplets over a region with opposite wetting properties, etc.

In some cases, two or more droplets may be fused, manipulated and/or coalesced using Couette shear cells, shaken emulsions, and/or membrane emulsification. In some embodiments, two or more droplets may be fused, manipulated and/or coalesced into one droplet using electric and/or magnetic fields, e.g., from one or more field-generating components contained within a substrate. Non-limiting examples of systems comprising a plurality of electric and/or magnetic field-generating components arranged to be able to interact and/or manipulate a sample are disclosed in U.S. patent application Ser. No. 11/105,322, filed Apr. 13, 2005, entitled "Methods and Apparatus for Manipulation and/or Detection of Biological Samples and Other Objects," by Ham, et al., published as U.S. Patent Application Publication No. 2006/0020371 on Jan. 26, 2006 (now abandoned), and International Patent Application No. PCT/US2008/007941, filed Jun. 26, 2008, entitled "Methods and Apparatus for Manipulation of Droplets", published as WO 2009/005680, each incorporated herein by reference.

The "cross-sectional dimension" of the channel is measured perpendicular to the direction of fluid flow. Most fluid channels in components of the invention have maximum cross-sectional dimensions less than 2 mm, and in some cases, less than 1 mm. In one set of embodiments, all fluid channels containing embodiments of the invention are microfluidic or have a largest cross sectional dimension of no more than 2 mm or 1 mm. In another embodiment, the fluid channels may be formed in part by a single component (e.g. an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channel(s) containing embodiments of the invention are less than 500 microns, less than 200 microns, less than 100 microns, less than 50 microns, or less than 25 microns.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

In one embodiment, a kit may be provided, containing one or more of the above compositions. A "kit," as used herein, typically defines a package or an assembly including one or more of the compositions of the invention, and/or other compositions associated with the invention, for example, as previously described. Each of the compositions of the kit may be provided in liquid form (e.g., in solution), in solid form (e.g., a dried powder), etc. A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

Non-limiting examples of microfluidic systems that may be used with the present invention are disclosed in U.S. patent application Ser. No. 11/246,911, filed Oct. 7, 2005, entitled "Formation and Control of Fluidic Species," published as U.S. Patent Application Publication No. 2006/0163385 on Jul. 27, 2006, now U.S. Pat. No. 9,038,919, issued May 26, 2015; U.S. patent application Ser. No. 11/024,228, filed Dec. 28, 2004, entitled "Method and Apparatus for Fluid Dispersion," published as U.S. Patent Application Publication No. 2005/0172476 on Aug. 11, 2005, now U.S. Pat. No. 7,708,949, issued May 4, 2010; U.S. patent application Ser. No. 11/360,845, filed Feb. 23, 2006, entitled "Electronic Control of Fluidic Species," published as U.S. Patent Application Publication No. 2007/000342 on Jan. 4, 2007, now U.S. Pat. No. 8,765,485 issued Jul. 1, 2014; International Patent Application No. PCT/US2006/007772, filed Mar. 3, 2006, entitled "Method and Apparatus for Forming Multiple Emulsions," published as WO 2006/096571 on Sep. 14, 2006; U.S. patent application Ser. No. 11/368,263, filed Mar. 3, 2006, entitled "Systems and Methods of Forming Particles," published as U.S. Patent Application Publication No. 2007/0054119 on Mar. 8, 2007 (now abandoned); U.S. Provisional Patent Application Ser. No. 60/920,574, filed Mar. 28, 2007, entitled "Multiple Emulsions and Techniques for Formation"; International Patent Application No. PCT/US2006/001938, filed Jan. 20, 2006, entitled "Systems and Methods for Forming Fluidic Droplets Encapsulated in Particles Such as Colloidal Particles," published as WO 2006/078841 on Jul. 27, 2006, each incorporated herein by reference; U.S. Application Ser. No. 61/008,862 entitled "Systems and Methods for Nucleic Acid Sequencing," filed Dec. 21, 2007; and U.S. Application Ser. No. 61/098,710 entitled "Systems and Methods for Nucleic Acid Sequencing," filed Sep. 19, 2008. Also incorporated herein by reference is International Patent Application No. PCT/US2008/013912, filed Dec. 19, 2008, entitled "Systems and Methods for Nucleic Acid Sequencing," by D. Weitz, et al., published as WO 2009/085215, and U.S. Provisional Application Ser. No. 61/139,207, entitled "Particle-Assisted Nucleic Acid Sequencing," filed on Dec. 19, 2008.

The following examples are intended to illustrate certain embodiments of the present invention, but do not exemplify the full scope of the invention.

EXAMPLE 1

Figure 7:
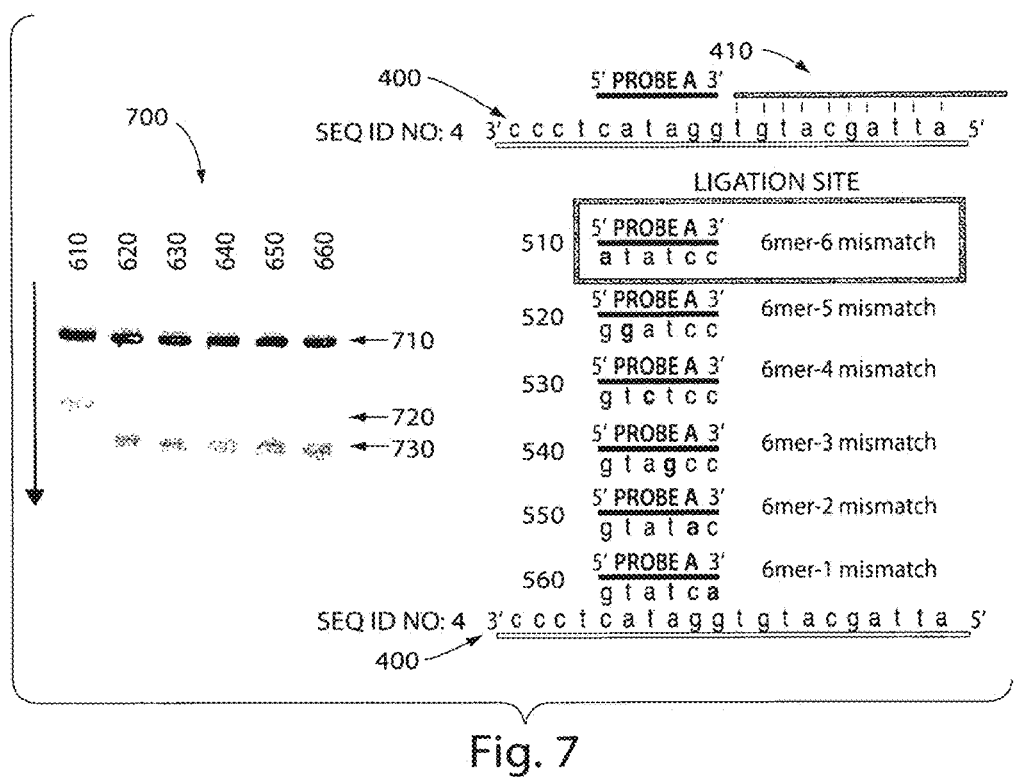
FIG. 7 shows an image of a PAGE gel and illustrations of nucleic acid probes and targets according to still another embodiment of the invention.

This example demonstrates single base-pair specificity of nucleic acid probes using a ligation test assay. Referring to FIG. 7, nucleic acid probe sequences 5'-ATATCC-3' 510; 5'-GGATCC-3' 520; 5'-GTCTCC-3' 530; 5'-GTAGCC-3' 540; 5'-GTATAC-3' 550; and 5'-GTATCA-3' 560 were separately mixed with target 400, probe 410, and ligase and incubated for 30 min at room temperature. Each reaction contained 20 microliters of 1× ligase buffer, 400 Units of T4 DNA ligase, 100 nM of a nucleic acid probe selected from nucleic acid probes 500-560, 200 nM of target 400, 100 nm of probe 410, and 1 mg/mL BSA. Following incubation, 20 microliters of a stop solution were added to quench the reaction. The stop solution contained 50 mM EDTA, 85% v/v formamide, and 0.005% bromophenol blue. The reactions were analyzed by denaturing polyacrylamide gel electrophoresis (PAGE) at 350 volts for 1 hour, stained with 1× SYBR Gold in TBE buffer, and visualized with UV light.

Probes 510 through 560 each have a single base pair mismatch with the target sequence 3'-ATAGG-5' as indicated by the underlined base above. In this system, each of probes 510 through 560 would be ligated to probe 410 if a stable duplex is formed. Referring to image 700, which shows the results denaturing PAGE separation of nucleic acids by molecular weight, lane 610 depicts the separation of a ligation reaction with probes 410 and 510, lane 620 depicts the separation of a ligation reaction with probes 410 and 520, lane 630 depicts the separation of a ligation reaction with probes 410 and 530, lane 640 depicts the separation of a ligation reaction with probes 410 and 540, lane 650 depicts the separation of a ligation reaction with probes 410 and 550, and lane 660 depicts the separation of a ligation reaction with probes 410 and 560. Position 710 indicates the position of target 400, position 720 indicates the position of ligation products of nucleic acid probes 510-560 and probe 410, and position 730 indicates the position of non-ligated probe 410. In lane 610, the amount of free ligation product greatly outweighed the amount of free probe 410 indicating that ligation of a 6-mer with a terminal mismatch occurred with relatively high efficiency but that some non-ligated probe 410 remained. Lane 620 shows a small amount of ligation product, and lanes 630 though 660 show that essentially no ligation occurred between probes 530 through 560 and probe 410, thereby demonstrating the ability of the probes in this particular example to discern nucleic acid probes containing a single mismatch from a nucleic acid containing no mismatches.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of at least partially determining the sequence of a target nucleic acid, the method comprising:
    passing a microfluidic droplet containing a target nucleic acid through a microfluidic channel;
    injecting a plurality of particles into the microfluidic droplet containing the target nucleic acid, at least some of the particles have nucleic acid probes fastened thereto that can hybridize with said target nucleic acid, and wherein the particles comprise a gel;
    hybridizing said nucleic acid probes to the target nucleic acid; and
    at least partially determining the sequence of the target nucleic acid.

2. The method of claim 1, wherein at least one of the particles is associated with at least one identification entity.

3. The method of claim 2, wherein said at least partially determining the sequence of the target nucleic acid comprises determining the at least one identification entity, wherein the at least one identification entity allows the sequences of the nucleic acid probe to be determined.

4. The method of claim 2, further comprising determining the at least one identification entity.

5. The method of claim 4, wherein the at least one identification entity comprises at least one fluorophore and the at least one identification entity is determined by detecting fluorescence from the at least one fluorophore.

6. The method of claim 1, wherein at least some of the nucleic acid probes contain at least six residues.

7. The method of claim 1, wherein at least some of the nucleic acid probes contain DNA.

8. The method of claim 1, wherein the target nucleic acid comprises DNA.

9. The method of claim 1, wherein the target nucleic acid comprises a signaling entity.

10. The method of claim 9, further comprising determining association of the target nucleic acid and at least some of the particles.

11. The method of claim 10, wherein said determining the association of the target nucleic acid and at least some of the particles comprises determining the signaling entity.

12. The method of claim 11, wherein the signaling entity is not covalently bound to the target nucleic acid.

13. The method of claim 1, further comprising amplifying the target nucleic acid.

14. The method of claim 1, wherein at least one of the nucleic acid probes is immobilized.

15. The method of claim 14, wherein the at least one identification entity comprises at least one fluorophore.

16. The method of claim 1, wherein the plurality of particles comprise at least 200 different nucleic acid probe sequences.

17. The method of claim 1, wherein the plurality of particles comprise at least 1000 different nucleic acid probe sequences.

18. The method of claim 1, wherein said at least partially determining the sequence of the target nucleic acid comprises sequencing by hybridization.

19. The method of claim 1, wherein said at least partially determining the sequence of the target nucleic acid comprises determining a hybridization spectrum comprising the sequences of the nucleic acid probes used for constructing a nucleic acid hybridized to the target nucleic acid after hybridizing said nucleic acid probes to the target nucleic acid.

20. The method of claim 1, wherein said at least partially determining the sequence of the target nucleic acid comprises determining the sequences of the nucleic acid probes after hybridizing said nucleic acid probes to the target nucleic acid.

* * * * *

SEQUENCE LISTING

```
<160> NUMBER OF SEQ ID NOS: 4

<210> SEQ ID NO 1
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 1
atccgcttta                                                          10

<210> SEQ ID NO 2
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 2
ctactaaagc ggat                                                     14

<210> SEQ ID NO 3
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 3
gtatccacat gc                                                       12

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
attagcatgt ggatactccc                                               20
```